US012187675B2

(12) United States Patent
Veryasov et al.

(10) Patent No.: US 12,187,675 B2
(45) Date of Patent: Jan. 7, 2025

(54) PROCESS TO CONDUCT AN ALKANE TRANSFORMATION INTO OLEFINS IN AN ELECTRIFIED FLUIDIZED BED REACTOR

(71) Applicant: TOTALENERGIES ONETECH, Courbevoie (FR)

(72) Inventors: Gleb Veryasov, Seneffe (BE); Walter Vermeiren, Seneffe (BE); Nikolai Nesterenko, Nivelles (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 18/710,414

(22) PCT Filed: Nov. 14, 2022

(86) PCT No.: PCT/EP2022/081736
§ 371 (c)(1),
(2) Date: May 15, 2024

(87) PCT Pub. No.: WO2023/094196
PCT Pub. Date: Jun. 1, 2023

(65) Prior Publication Data
US 2024/0327317 A1 Oct. 3, 2024

(30) Foreign Application Priority Data
Nov. 25, 2021 (EP) ..................................... 21315247

(51) Int. Cl.
*C07C 5/46* (2006.01)
*B01J 8/18* (2006.01)
(Continued)

(52) U.S. Cl.
CPC ............... *C07C 5/46* (2013.01); *B01J 8/1827* (2013.01); *B01J 8/1836* (2013.01); *B01J 8/42* (2013.01);
(Continued)

(58) Field of Classification Search
CPC ......... C07C 5/46; C07C 5/42; C07C 2521/12; C07C 2523/04; C07C 2523/14; B01J 8/1827; B01J 8/1836; B01J 8/42
See application file for complete search history.

(56) References Cited

U.S. PATENT DOCUMENTS 2,982,622 A    5/1961  Jahnig et al.
3,499,947 A *  3/1970  Johnson ..................... B01J 8/42
                                                        585/602
(Continued)

FOREIGN PATENT DOCUMENTS

WO    2022023365 A1    2/2022

OTHER PUBLICATIONS

Al-Zahrani Saeed et al, "Effects of carbon dioxide during oxidative coupling of methane over lithium/magnesia: mechanisms and models", Industrial & Engineering Chemistry Research, vol. 33, No. 2, Feb. 1, 1994, pp. 251-258.
(Continued)

*Primary Examiner* — Thuan D Dang
(74) *Attorney, Agent, or Firm* — Ewing & Jones, PLLC

(57) ABSTRACT

The disclosure concerns a process to perform a reaction of alkane transformation into olefins, said process comprising the steps of (a) providing a stream of light alkane-comprising feedstock with one or more alkanes and one or more oxidants selected from $CO_2$ and/or COS; and providing at least one fluidized bed reactor comprising at least two electrodes and a bed comprising particles; (b) putting the particles of the bed in a fluidized state to obtain a fluidized bed; and (c) heating the fluidized bed to a temperature ranging from 600° C. to 1500° C. to conduct the reaction; the process is remarkable in that the step c) is performed by passing an electric current through the fluidized bed; the particles of the bed comprise electrically conductive particles, and in that, at least 10 wt. % of the particles are
(Continued)

electrically conductive particles and have a resistivity ranging from 0.001 to 500 Ohm·cm at 800° C.

13 Claims, 3 Drawing Sheets

(51) Int. Cl.
   *B01J 8/42* (2006.01)
   *C07C 5/42* (2006.01)
(52) U.S. Cl.
   CPC ....... *C07C 5/42* (2013.01); *B01J 2208/00398* (2013.01); *C07C 2521/12* (2013.01); *C07C 2523/04* (2013.01); *C07C 2523/14* (2013.01)

(56) References Cited

U.S. PATENT DOCUMENTS

| | | |
|---|---|---|
| 3,787,517 A | 1/1974 | Haag et al. |
| 2021/0051770 A1 | 2/2021 | Appel et al. |

OTHER PUBLICATIONS

Bülow M et al, "The mutual transformation of hydrogen sulphide and carbonyl sulphide and its role for gas desulphurization processes with zeolitic molecular sieve sorbents", "Studies in surface science and catalysis vol. 120 Part A", pp. 301-345, 1999, Elsevier Science B.V.

Assirey Eman Abdul Rahman Ed et al., "Perovskite synthesis, properties and their related biochemical and industrial application", Saudi Pharmaceutical Journal, Elsevier, Amsterdam, NL, May 14, 2019, vol. 27, No. 6, pp. 817-829.

Cailin Tang et al., "Roles of oxygen and carbon dioxide on methane oxidative coupling over CaO and Sm2O3 catalysts", Applied Catalysis A: General, vol. 115, No. 2, Aug. 1, 1994, pp. 243-256.

International Search Report and Written Opinion issued in Application No. PCT/EP2022/081736, dated Feb. 15, 2023, 16 pages.

International Preliminary Report on Patentability issued in Application No. PCT/EP2022/081736, dated Feb. 26, 2024, 22 pages.

Allison M. Arinaga et al., "Alternative Oxidants for the Catalytic Oxidative Coupling of Methane", Angewandte Chemie, vol. 60, Issue 19, 2021, 15 Pages.

Qingjun Zhu et al., "Sulfur as a selective 'soft' oxidant for catalytic methane conversion probed by experiment and theory", Nature Chemistry, vol. 5, 2013, pp. 104-109.

Sivaram Pradhan et al., "Partial oxidation of propane with CO2 on Ru doped catalysts", Catalysis Science and Technology, Issue 6, 2016, 11 pages.

C.K. Gupta, Ph.D., et al., Fluid Bed Technology in Materials Processing, 1999 by CRC Press, 512 pages.

Young-Wook Kim et al., "Effect of grain growth on electrical properties of silicon carbide ceramics sintered with gadolinia and yttria", Journal of the European Ceramic Society, vol. 35, Issue 15, Dec. 2015, pp. 4137-4142.

Kwang Joo Kim et al., "Effects of M2O3—Y2O3 (M=Sc and Al) additives on electrical conductivity of hot-pressed SiC ceramics", Ceramics International, vol. 46, Issue 4, Mar. 2020, pp. 5454-5458.

P.R. Gunjal, V.V. Ranade, "Catalytic Reaction Engineering", Industrial Catalytic Processes for Fine and Specialty Chemicals, (2016) 314 pages.

\* cited by examiner

PROCESS TO CONDUCT AN ALKANE TRANSFORMATION INTO OLEFINS IN AN ELECTRIFIED FLUIDIZED BED REACTOR

CROSS-REFERENCE TO RELATED APPLICATIONS

This application claims the benefit of PCT/EP2022/081736 filed Nov. 14, 2022, which claims priority from EP 21315247.3 filed Nov. 25, 2021, which are incorporated herein by reference in their entireties for all purposes.

FIELD OF THE DISCLOSURE

The present disclosure relates to a process for performing an alkane transformation into olefins, such as an alkane partial oxidation and/or oxidative coupling of alkanes, in a fluidized bed reactor wherein the reaction is performed without the need of an external heating device in the said fluidized bed reactor. The present disclosure aims to contribute to the replacement of the use of fossil carbon-based fuels heating devices. The present disclosure relates to the electrification of the chemical industry.

TECHNICAL BACKGROUND

Climate change and ongoing energy transition make it mandatory to develop new electrified processes to produce, among others, base chemicals. Given the development of shale gas exploitation, conversion of light alkanes into alkenes (or olefins) is one of the possible cleaner opportunities for the reduction of dependence on crude-based products.

Alkene hydrocarbons within the petrochemical industry and can include any unsaturated hydrocarbon compound containing at least one carbon-to-carbon double bond. Alkenes are used widely within the chemical industry for their general reactivity and ability to polymerize or oligomerize into longer chain hydrocarbon products such as synthetic fuels.

Today short-chain alkenes are typically produced using gaseous or liquid light hydrocarbons which are steam-cracked at temperatures of 750° C. to 950° C. The cracked gas contains multiple alkene hydrocarbons and is immediately quenched to halt the numerous secondary (olefin-consuming) free radical reactions within the off-gas. The various alkenes can then be separated from the remaining quenched cracked gas via distillation.

Natural gas is a naturally occurring mixture of hydrocarbon gases including methane and contains up to about twenty percent concentration of higher hydrocarbons such as ethane and impurities such as carbon dioxide and hydrogen sulphide. With hundreds of years and trillions of cubic feet of proven, unextracted, natural gas reserves, natural gas potentially provides a rich source of hydrocarbons. Unfortunately, natural gas, or more specifically the methane found in natural gas is expensive to transport for extended distances except by pipeline. Even with the use of pipelines, methane requires significant capital investment in the pipeline itself and incurs significant operational expense in the recompression stations needed to maintain a reasonable pipeline flow. However, restricting transport to pipelines essentially relegates such methane sources to the role of a regional supply, meaning that unless a local demand exists for the methane, the natural gas supply is "stranded"-available for extraction but without a local demand making the extraction economically attractive and practical.

Historically methane has been converted to longer chain hydrocarbons through steam reforming to provide a synthesis gas ("syn-gas"), containing a mixture of carbon monoxide and hydrogen, which is then used as a feedstock to a Fischer-Tropsch process which converts the carbon monoxide and hydrogen into liquid hydrocarbons (often referred to as a "gas-to-liquids" or "GTL" process). Stream reforming could handle as well higher alkanes (e.g., ethane and propane) and has numerous commercialized options. However, even with Fischer-Tropsch, the ability to convert methane to short-chain alkenes such as ethylene is extremely limited.

The oxidative coupling of methane ("OCM") reaction promotes the formation of alkene hydrocarbons such as ethylene using an exothermic reaction of methane and oxygen over one or more catalysts according to the following equation:

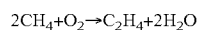

$$2CH_4 + O_2 \rightarrow C_2H_4 + 2H_2O$$

The reaction is exothermic and historically is conducted at very high temperatures of above 750° C. Difficulties related to the control of reaction drives seek alternative oxidants. Suitable alternatives involve compounds like $N_2O$, $S_2$ (a gaseous form of sulphur, $S_8$), $CO_2$, which were mentioned in the academic literature (Angewandte Chemie, Volume 60, Issue 19, 2021, Pages 10502-10515; and Nature Chemistry, Volume 5, 2013, Pages 104-109).

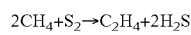

$$2CH_4 + S_2 \rightarrow C_2H_4 + 2H_2S$$

Conversion of higher alkanes accompanying methane in NG reservoirs through oxidative dehydrogenation stumbles the same issues as oxidative coupling of methane (Catalysis Science and Technology, Issue 6, 2016, Pages 5483-5493).

The present disclosure aims to provide a large-scale solution to one or more of the problems encountered in the prior art that is suitable for application in the industry, such as the chemical industry. The present disclosure aims to contribute to the replacement of the use of fossil carbon-based fuels heating devices in fluidized bed reactors. The present disclosure provides a solution to conduct an alkane transformation into olefins in a fluidized bed reactor, such as an alkane partial oxidation reaction and/or an oxidative coupling of light alkane reaction.

SUMMARY OF THE DISCLOSURE

According to a first aspect, the disclosure provides for a process to perform an alkane transformation into olefin, said process comprising the steps of:
 a) providing a stream of a light alkane-comprising feedstock comprising one or more alkanes and one or more oxidants selected from carbon dioxide ($CO_2$), carbonyl sulphide (COS) and any mixture thereof; and further providing at least one fluidized bed reactor comprising at least two electrodes and a bed comprising particles;
 b) putting the particles of the bed in a fluidized state to obtain a fluidized bed; and
 c) heating the fluidized bed to a temperature ranging from 600° C. to 1500° C. to conduct the alkane transformation into olefin on the light alkane-comprising feedstock;
 d) optionally, recovering the products of the reaction;
the process is remarkable in that the step c) of heating the fluidized bed is performed by passing an electric current through the fluidized bed; in that the particles of the bed comprise electrically conductive particles and optional particles of a catalytic composition; and in that, at least 10 wt. % of the particles based on the total weight of the particles of the bed are electrically conductive particles and have a resistivity ranging from 0.001 Ohm·cm to 500 Ohm·cm at 800° C.

With preference, the alkane transformation into olefin is or comprises an alkane partial oxidation reaction and/or an oxidative coupling reaction of light alkanes.

Surprisingly, it has been found that the use of electrically conductive particles in one or more fluidized bed reactors which are electrified, allows attaining and maintaining a temperature sufficient to carry out an alkane partial oxidation reaction and/or an oxidative coupling reaction on light alkanes. Although these reactions are requesting high-temperature conditions such as temperature conditions ranging from 600° C. to 1500° C., the reaction is conducted without the need of another external heating device such as heating means in or surrounding the reactor vessel of the fluidized bed reactor. The use of at least 10 wt. % of electrically conductive particles within the particles of the bed allows minimizing the loss of heat when a voltage is applied. Thanks to the Joule effect, most, if not all, the electrical energy is transformed into heat that is used for the heating of the reactor medium.

For example, the electrically conductive particles are or comprise one or more selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

In a preferred embodiment, the electrically conductive particles are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphides being doped with one or more lower-valent cations, and any mixture thereof.

Advantageously, said process further comprises a step d) of recovering the products of the reaction wherein said products comprise one or more olefins and carbon monoxide. Step d) is performed after step c).

In a preferred embodiment, the volumetric heat generation rate is greater than 0.1 MW/m³ of fluidized bed, more preferably greater than 1 MW/m³, in particular, greater than 3 MW/m³.

In a preferred embodiment, at least one fluidized bed reactor is devoid of heating means. It is understood that at least one fluidized bed reactor is devoid of heating means other than the combination of the electrodes and the bed comprising at least 10 wt. % of electrically conductive particles. For example, at least one fluidized bed reactor comprises a vessel and is devoid of heating means located around or inside the vessel. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

For example, the content of electrically conductive particles is ranging from 10 wt. % to 100 wt. % based on the total weight of the particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the content of electrically conductive particles based on the total weight of the bed is at least 12 wt. % based on the total weight of the particles of the bed; preferably, at least 15 wt. %, more preferably, at least 20 wt. %; even more preferably at least 25 wt. %, and most preferably at least 30 wt. % or at least 40 wt. % or at least 50 wt. % or at least 60 wt. %.

For example, the electrically conductive particles have a resistivity ranging from 0.005 to 400 Ohm·cm at 800° C., preferably ranging from 0.01 to 300 Ohm·cm at 800° C.; more preferably ranging from 0.05 to 150 Ohm·cm at 800° C. and most preferably ranging from 0.1 to 100 Ohm·cm at 800° C.

For example, the electrically conductive particles have a resistivity of at least 0.005 Ohm·cm at 800° C.; preferably of at least 0.01 Ohm·cm at 800° C., more preferably of at least 0.05 Ohm·cm at 800° C.; even more preferably of at least 0.1 Ohm·cm at 800° C., and most preferably of at least 0.5 Ohm·cm at 800° C.

For example, the electrically conductive particles have a resistivity of at most 400 Ohm·cm at 800° C.; preferably of at most 300 Ohm·cm at 800° C., more preferably of at most 200 Ohm·cm at 800° C.; even more preferably of at most 150 Ohm·cm at 800° C., and most preferably of at most 100 Ohm·cm at 800° C. The selection of the content of electrically conductive particles based on the total weight of the particles of the bed and of the electrically conductive particles of a given resistivity influence the temperature reached by the fluidized bed. Thus, in case the targeted temperature is not attained, the person skilled in the art may increase the density of the bed of particles, the content of electrically conductive particles based on the total weight of the particles of the bed and/or select electrically conductive particles with a lower resistivity to increase the temperature reach by the fluidized bed.

For example, the density of the bed of particles is expressed as the void fraction. Void fraction or bed porosity is the volume of voids between the particles divided by the total volume of the bed. At the incipient fluidisation velocity, the void fraction is typically between 0.4 and 0.5. The void fraction can increase up to 0.98 in fast fluidised beds with lower values at the bottom of about 0.5 and higher than 0.9 at the top of the bed. The void fraction can be controlled by the linear velocity of the fluidising gas and can be decreased by recycling solid particles that are recovered at the top and send back to the bottom of the fluidized bed, which compensates for the entrainment of solid particles out of the bed.

The void fraction VF is defined as the volume fraction of voids in a bed of particles and is determined according to the following equation:

$$VF = \frac{Vt - Vp}{Vt} \qquad (1)$$

wherein Vt is the total volume of the bed and is determined by $$Vt = AH \qquad (2)$$

wherein A is the cross-sectional area of the fluidized bed and H is the height of the fluidized bed; and wherein Vp is the total volume of particles within the fluidized bed.

For example, the void fraction of the bed is ranging from 0.5 to 0.8; preferably ranging from 0.5 to 0.7, more preferably from 0.5 to 0.6. To increase the density of the bed of particles, the void fraction is to be reduced.

For example, the particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

Determination by sieving according to ASTM D4513-11 is preferred. In case the particles have an average size of below 20 μm the determination of the average size can also be done by Laser Light Scattering according to ASTM D4464-15.

For example, the electrically conductive particles of the bed have an average particle size ranging from 5 to 300 μm as determined by sieving according to ASTM D4513-11, preferably ranging from 10 to 200 μm and more preferably ranging from 30 to 150 μm.

With preference, the electrically conductive particles of the bed are or comprise one or more selected from graphite, carbon black, one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the electrically conductive particles of the bed are or comprise one or more carbon-containing particles being graphite.

With preference, the electrically conductive particles of the bed are or comprise one or more selected from graphite, carbon black, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the electrically conductive particles of the bed are or comprise one or more selected from one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are devoid of one or more carbon-containing particles selected from petroleum coke, carbon black, coke or a mixture thereof.

In an embodiment, the electrically conductive particles of the bed are devoid of one or more carbon-containing particles selected from graphite, petroleum coke, carbon black, coke or a mixture thereof. For example, the electrically conductive particles of the bed are devoid of graphite and/or carbon black. For example, the electrically conductive particles of the bed are devoid of petroleum coke and/or coke.

Alternatively, the electrically conductive particles of the bed are or comprise graphite and one or more selected from one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

As an alternative, the electrically conductive particles of the bed are one or more particles selected from one or more metallic alloys, one or more non-metallic resistors provided that the non-metallic resistor is not silicon carbide, one or more metallic carbides, one or more transition metal nitrides, one or more metallic phosphides, graphite, carbon black, one or more superionic conductors, one or more phosphate electrolytes, one or more mixed oxides being doped with one or more lower-valent cations and/or one or more and/or mixed sulphides being doped with one or more lower-valent cations and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, graphite, carbon black, one or more mixed oxides being doped with one or more lower-valent cations, one or more mixed sulphides being doped with one or more lower-valent cations, and any mixture thereof with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise graphite and one or more selected from one or more metallic alloys, one or more non-metallic resistors, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more non-metallic resistors, one or more mixed oxides being doped with one or more lower-valent cations, one or more mixed sulphides being doped with one or more lower-valent cations, and any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

Advantageously, the electrically conductive particles of the bed comprise one or more metallic alloys. For example, said one or more metallic alloys are selected from Ni—Cr, Fe—Ni—Cr, Fe—Ni—Al or a mixture thereof. With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0 mol. % based on the total molar content of the said metallic alloy, preferably at most 1.5 mol. %, more preferably at most 1.0 mol. %, even more preferably at most 0.5 mol. %.

For example, said one or more non-metallic resistors are selected from silicon carbide (SiC), molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof, preferably silicon carbide.

For example, said one or more metallic carbides are selected from iron carbide ($Fe_3C$) and/or molybdenum carbide (such as a mixture of MoC and $Mo_2C$).

For example, said one or more transition metal nitrides are selected from zirconium nitride (ZrN), tungsten nitride (such as a mixture of $W_2N$, WN, and $WN_2$), vanadium nitride (VN), tantalum nitride (TaN), and/or niobium nitride (NbN).

For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

Advantageously, the electrically conductive particles of the bed comprise one or more superionic conductors. For example, said one or more superionic conductors are selected from $LiAlSiO_4$, $Li_{10}GeP_2S_{12}$, $Li_{3.6}Si_{0.6}P_{0.4}O_4$, sodium superionic conductors (NaSICON), such as $Na_3Zr_2PSi_2O_{12}$, or sodium beta alumina, such as $NaAl_{11}O_{17}$, $Na_{1.6}Al_{11}O_{17.3}$, and/or $Na_{1.76}Li_{0.38}Al_{10.62}O_{17}$.

For example, said one or more phosphate electrolytes are selected from $LiPO_4$ or $LaPO_4$.

For example, said one or more mixed oxides are ionic or mixed conductors being doped with one or more lower-valent cations. Advantageously, said mixed oxides are doped with one or more lower-valent cations, and are selected from oxides having a cubic fluorite structure, perovskite, pyrochlore.

For example, said one or more mixed sulphides are ionic or mixed conductors being doped with one or more lower-valent cations.

For example, the electrically conductive particles of the bed are or comprise one or more non-metallic resistors selected from silicon carbide, molybdenum disilicide or a mixture thereof. For example, the electrically conductive particles of the bed are or comprise silicon carbide.

For example, the electrically conductive particles of the bed are or comprise a mixture of a non-metallic resistor being silicon carbide and electrically conductive particles different from silicon carbide. The presence of electrically conductive particles different from silicon carbide in the bed is optional. It can be present as a starting material for heating the bed since it was found that the resistivity of silicon carbide at room temperature is too high to start heating the bed. Alternatively to the presence of electrically conductive particles different from silicon carbide, it is possible to provide heat to the reactor for a defined time to start the reaction.

For example, the silicon carbide is selected from sintered silicon carbide, nitride-bounded silicon carbide, recrystallised silicon carbide, reaction bonded silicon carbide and any mixture thereof.

For example, the electrically conductive particles of the bed are or comprise a mixture of a non-metallic resistor being silicon carbide and electrically conductive particles different from silicon carbide. With preference, the electrically conductive particles of the bed comprise from 10 wt. % to 99 wt. % of silicon carbide based on the total weight of the electrically conductive of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed are or comprise a mixture of a non-metallic resistor being silicon carbide and electrically conductive particles different from silicon carbide and the said electrically conductive particles different from silicon carbide are one or more carbon-containing particles and/or one or more mixed oxides being doped with one or more lower-valent cations and/or one or more mixed sulphides being doped with one or more lower-valent cations.

For example, the electrically conductive particles of the bed are or comprise a mixture of a non-metallic resistor being silicon carbide and electrically conductive particles different from silicon carbide and the said electrically conductive particles different from silicon carbide are graphite and/or one or more mixed oxides being doped with one or more lower-valent cations and/or one or more mixed sulphides being doped with one or more lower-valent cations.

For example, the electrically conductive particles of the bed are or comprise one or more mixed oxides being ionic conductor, namely being doped with one or more lower-valent cations; with preference, the mixed oxides are selected from:

one or more oxides having a cubic fluorite structure being at least partially substituted with one or more lower-valent cations, preferentially selected from Sm, Gd, Y, Sc, Yb, Mg, Ca, La, Dy, Er, Eu; and/or one or more $ABO_3$-perovskites with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or one or more $ABO_3$-perovskites with A bivalent cation and B tetra-valent cation, being at least partially substituted with one or more lower-valent cations, preferentially selected from magnesium (Mg), scandium (Sc), yttrium (Y), neodymium (Nd) or ytterbium (Yb) in the B position or with a mixture of different B elements in the B position; and/or.

one or more $A_2B_2O_7$-pyrochlores with A trivalent cation and B tetra-valent cation being at least partially substituted in A position with one or more lower-valent cations, preferentially selected from Ca or Mg, and comprising at least one of Sn, Zr and Ti in B position.

For example, the electrically conductive particles of the bed are or comprise one or more mixed sulphides being ionic conductor, namely being doped with one or more lower-valent cations; with preference, the mixed sulphides are selected from:

one or more sulphides having a cubic fluorite structure being at least partially substituted with one or more lower-valent cations, preferentially selected from Sm, Gd, Y, Sc, Yb, Mg, Ca, La, Dy, Er, Eu; and/or one or more $ABS_3$ structures with A and B tri-valent cations being at least partially substituted in A position with one or more lower-valent cations, preferably selected from Ca, Sr, or Mg and comprising at least one of Ni, Ga, Co, Cr, Mn, Sc, Fe and/or a mixture thereof in B position; and/or one or more $ABS_3$ structures with A bi-valent cation and B tetra-valent cation, being at least partially substituted with one or more lower-valent cations, preferably selected from Mg, Sc, Y, Nd or Yb in the B position or with a mixture of different B elements in the B position; and/or one or more $A_2B_2S_7$ structures with A tri-valent cation and B tetra-valent cation, being at least partially substituted in A position with one or more lower-valent cations, preferably selected from Ca or Mg, and comprising at least one of Sn, Zr and Ti in B position.

With preference, the degree of substitution in the one or more mixed oxides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed oxides doped with one or more lower-valent cations is between 1 and 50 atom % based on the total number of atoms present in the one or more $ABO_3$-perovskites with A and B tri-valent cations, in the one or more $ABO_3$-perovskites with A bivalent cation and B tetra-valent cation or in the one or more $A_2B_2O_7$-pyrochlores with A trivalent cation and B tetra-valent cation respectively, preferably between 3 and 20 atom %, more preferably between 5 and 15 atom %.

With preference, the degree of substitution in the one or more mixed sulphides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed sulphides doped with one or more lower-valent cations is between 1 and 50 atom % based on the total number of atoms present in the one or more $ABS_3$ structures with A and B tri-valent cations, in the one or more $ABS_3$ structures with A bivalent cation and B tetra-valent cation or in the one or more $A_2B_2S_7$ structures with A trivalent cation and B tetra-valent cation respectively, preferably between 3 and 20 atom %, more preferably between 5 and 15 atom %.

For example, the electrically conductive particles of the bed are or comprise one or more metallic alloys; with preference, one or more metallic alloys are selected from Ni—Cr, Fe—Ni—Cr, Fe—Ni—Al or a mixture thereof.

With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0 mol. % based on the total molar content of the said metallic alloy, preferably at most 1.5 mol. %, more preferably at most 1.0 mol. %, even more preferably at most 0.5 mol. %.

For example, the electrically conductive particles of the bed are or comprise a mixture of a non-metallic resistor being silicon carbide and particles different from silicon carbide wherein the particles different from silicon carbide are or comprise graphite.

For example, the electrically conductive particles of the bed are or comprise one or more carbon-containing particles being graphite. With preference, said graphite is graphite particles having an average particle size ranging from 5 to 300 μm as determined by sieving according to ASTM D4513-11, more preferably ranging from 10 to 200 μm and most preferably ranging from 30 to 150 μm.

For example, the electrically conductive particles of the bed are or comprise graphite and one or more electrically conductive particles different from graphite and selected from one or more selected from one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, or any mixture thereof. With preference, the electrically conductive particles of the bed comprise from 10 wt. % to 99 wt. % of graphite based on the total weight of the electrically conductive of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

Advantageously, the bed comprises particles of a catalytic composition and the catalyst composition comprises one or more selected from rare earth oxides, rare earth sulphides, transition metal oxides transition metal sulphides and any mixture thereof and the catalyst composition optionally comprises one or more dopants. With preference, the one or more dopants comprise at least one alkali, alkali-earth, transition metal, post-transition metal or rare earth metal carbonate or thiocarbonate, or any mixture thereof.

Advantageously, the bed comprises particles of a catalytic composition and in that the catalyst composition comprises one or more selected from Na—W—Mn/$SiO_2$, NaCl—MnNa$_2$WO$_4$/$SiO_2$, $La_2O_3$—$CeO_2$, Li/MgO, CaO—$Sm_2O_3$, KCl—SmCl$_3$, CaO—NaCl/Na$_2$CO$_3$, $CeO_2$/ZnO, $La_2O_3$/$Al_2O_3$ and FeS$_x$.

For example, the alkane partial oxidation reaction and/or oxidative coupling reaction is conducted at a temperature ranging from 500° C. to 2000° C., more preferably from 550° C. to 1700° C., even more preferably from 600° C. to 1500° C., or from 700 to 1300° C.; most preferably from 800° C. to 1200° C. or from 900° C. to 1400° C.; and even most preferably from 1000° C. to 1500° C.

For example, the alkane partial oxidation reaction and/or oxidative coupling reaction is performed at a pressure ranging between 0.1 MPa and 10 MPa, preferably between 0.1 MPa and 5.0 MPa or between 0.2 MPa and 3.0 MPa.

In an embodiment, said process comprises a step of pre-heating with a gaseous stream said fluidized bed reactor before conducting the alkane partial oxidation reaction and/or oxidative coupling reaction in the fluidized bed reactor; with preference, said gaseous stream is a stream of inert gas and/or has a temperature comprised between 400° C. and 1000° C. The said embodiment is of interest when the particles of the bed such as silicon carbide have too high resistivity at room temperature to start the electro-heating of the bed.

For example, the alkane partial oxidation reaction and/or the oxidative coupling reaction is conducted in presence of a dilution stream and is performed at a weight hourly space velocity of said reaction stream comprised between 0.1 h$^{-1}$ and 100 h$^{-1}$, preferably comprised between 1.0 h$^{-1}$ and 50 h$^{-1}$. The weight hourly space velocity is defined as the ratio of mass flow of the reaction stream to the mass of solid particulate material in the fluidized bed.

The light alkane-comprising feedstock for the present process comprises one or more selected from natural gas and/or biogas. The light alkane-comprising feedstock for the present process comprises one or more alkanes selected from methane, ethane, propane, butane, iso-butane and any mixture thereof. The light alkane-comprising feedstock further comprises one or more oxidants selected from COS (carbonyl sulphide), $CO_2$ (carbon dioxide) and any mixture thereof. In an embodiment the step of providing a stream comprising light alkane-comprising feedstock comprising one or more alkanes and one or more oxidants comprise mixing a stream comprising one or more alkanes selected from methane, ethane, propane, butane, iso-butane and any mixture thereof; with a stream comprising one or more oxidants selected from COS (carbonyl sulphide), $CO_2$ (carbon dioxide) and any mixture thereof. Said mixing can be made outside the at least one fluidized bed reactor or in situ (i.e. inside the at least one fluidized bed reactor).

For example, COS could be produced by the techniques known in the art from the acid gas components ($H_2S$ and $CO_2$) present in natural gas reservoirs or biogas digesters.

In an embodiment, step a) comprises a sub-step of production of a COS-containing stream, wherein said sub-step comprises providing feedstream containing at least 30 wt. % of carbon dioxide ($CO_2$) and at least 20 wt. % of hydrogen sulphide ($H_2S$) based on the total weight of said feedstream and converting said feedstream into a COS-containing stream; wherein the conversion is performed at a temperature ranging from 50 to 800° C., at a pressure ranging from 0.01 to 5 MPa (from 0.1 to 50 bar) and at a GHSV ranging from 0.1 to 10 h$^{-1}$ wherein the COS-containing stream is containing water and at least 10 wt. % of carbonyl sulphide (COS) based on the total weight of said COS-containing stream; with preference, the sub-step of production of a COS-containing stream is performed in presence of a COS-conversion catalyst and at least one sorbent.

For example, in step b) the particles of the bed are put in a fluidized state by passing upwardly through the said bed a gaseous stream comprising a light alkane-containing feedstock. For example, in step b) the particles of the bed are put in a fluidized state by passing upwardly through the said bed a gaseous stream comprising methane. For example, the light alkane-containing feedstock is a methane feedstock.

In particular, the olefins obtained in the present process may include one or more alkene selected from ethylene, propylene, butylene, iso-butylene or any mixture thereof.

In a preferred embodiment, the residence time of the alkane-comprising feedstock in the fluidised bed section of the reactor where the temperature is between 600 and 1500° C., may range from 0.01 to 5.0 seconds, preferably from 0.1 to 1.0 seconds.

For example, the step of heating the fluidized bed is performed by passing an electric current at a voltage of at most 300 V through the fluidized bed, preferably at most 200 V, more preferably at most 150 V, even more preferably at most 120 V, most preferably at most 100 V, even most preferably at most 90 V.

For example, said process comprises a step of pre-heating with a gaseous stream the one or more fluidized bed reactor before conducting said alkane partial oxidation reaction and/or oxidative coupling reaction in the fluidized bed reactor; with preference, said gaseous stream is a stream of inert gas and/or has a temperature comprised between 400° C. and 1000° C.

For example, wherein the at least one fluidized bed reactor provided in step a) comprises a heating zone and a reaction zone and wherein the step c) of heating the fluidized bed to a temperature ranging from 600° C. to 1500° C. to conduct the alkane partial oxidation reaction and/or the oxidative coupling reaction comprises the following sub-steps:

heating the fluidized bed to a temperature ranging from 600° C. to 1500° C. by passing an electric current through the heating zone of the at least one fluidized bed, transporting the heated particles from the heating zone to the reaction zone, in the reaction zone, putting the heated particles in a fluidized state by passing upwardly through the said bed of the reaction zone a stream comprising a light alkane-comprising feedstock and optional diluent gases to obtain a fluidized bed to conduct the alkane transformation into olefin on the light alkane-comprising feedstock, optionally, recovering the particles from the reaction zone and recycling them to the heating zone.

For example, wherein the at least one fluidized bed reactor provided in step a) comprises a heating zone and a reaction zone and the step c) of heating the fluidized bed to a temperature ranging from 600° C. to 1500° C. to conduct the alkane partial oxidation reaction and/or the oxidative coupling reaction comprises the following sub-steps:

pre-heating the fluidized bed to ranging from 400° C. and 1000° C. by passing upwardly through the particles bed a fluidizing stream being a gaseous stream having a temperature ranging from 400° C. and 1000° C.;

heating the fluidized bed to a temperature ranging from 600° C. to 1500° C. by passing an electric current through the heating zone, transporting the heated particles from the heating zone to the reaction zone, in the reaction zone, putting the heated particles in a fluidized state by passing upwardly through the said bed of the reaction zone a stream comprising a light alkane-comprising feedstock and optional diluent gases to obtain a fluidized bed to conduct the alkane transformation into olefin on the light alkane-comprising feedstock, optionally, recovering the particles from the reaction zone and recycling them to the heating zone.

Thus, preferably, the particles are pre-heated and/or heated before step c) in a pre-heating zone and/or in a heating zone, so that:

the at least one fluidized bed reactor provided in step a) comprises a pre-heating zone wherein the step of pre-heating is performed by passing upwardly through the said bed a gaseous stream wherein the gaseous stream is provided to the pre-heating zone and wherein the gaseous stream used has a temperature ranging from 400° C. and 1000° C.; and/or the at least one fluidized bed reactor provided in step a) comprises a heating zone and a reaction zone, wherein the particles of the bed are put in a fluidized state in the heating zone by passing upwardly through the said bed a gaseous stream having a temperature ranging from 400° C. and 1000° C., and wherein the fluidized bed is heated to a temperature ranging from 600° C. to 1500° C. by passing an electric current through the heating zone.

The fluidizing stream may be a gaseous stream comprising one or more diluents, for example, one or more inert gas.

Step c) provides that the alkane transformation into olefin, such as the alkane partial oxidation reaction and/or oxidative coupling reaction, is performed on a light alkane-comprising feedstock which implies that a light alkane-comprising feedstock is provided.

For example, in step b) the particles of the bed are put in a fluidized state by passing upwardly through the said bed a gaseous stream and when the heating zone and the reaction zone are mixed (i.e. the same zone); said gaseous stream (i.e. the fluidizing stream) may be or comprise a light alkane-comprising feedstock.

For example, in step b) the particles of the bed are put in a fluidized state by passing upwardly through the said bed a gaseous stream and when the heating zone and the reaction zone are separated zones, the gaseous stream (i.e. the fluidizing stream) provided to the heating zone can be devoid of a light alkane-comprising feedstock. For example, in step b) the particles of the bed are put in a fluidized state by passing upwardly through the said bed a gaseous stream and the process comprises providing at least one fluidized bed reactor being a heating zone and at least one fluidized bed reactor being a reaction zone, the gaseous stream provided in step b) to the heating zone is devoid of a light alkane-comprising feedstock and the gaseous stream provided to the reaction zone comprises the light alkane-comprising feedstock.

It is understood that the light alkane-comprising feedstock is provided to the reaction zone and that when the heating zone is separated from the reaction zone, no light alkane-comprising feedstock is provided to the heating zone.

Advantageously, the products of the reaction comprise one or more olefins and carbon monoxide.

According to a second aspect, the disclosure provides an installation to perform an alkane transformation into olefin, according to at least one embodiment of the first aspect remarkable in that the installation comprises a $CO_2$ sulphuration unit comprising one or more conversion reactors, an optional separation unit, an electrified fluidized bed unit comprising at least one fluidized bed reactor comprising: at least two electrodes; a reactor vessel; one or more fluid nozzles for the introduction of a fluidizing gas and/or of a stream of light alkane-comprising feedstock within at least one fluidized bed reactor; and a bed comprising particles; wherein at least 10 wt. % of the particles of the bed based on the total weight of the particle of the bed are electrically conductive have a resistivity ranging from 0.001 Ohm·cm to 500 Ohm·cm at a temperature of 800° C.;

and in that wherein the $CO_2$ sulphuration unit, the separation unit when present and the electrified fluidized bed unit are fluidically connected in series in the order mentioned. This is when the process to perform an alkane transformation into olefin also comprises a sub-step of production of a COS-containing stream.

With preference, the alkane transformation into olefin is or comprises an alkane partial oxidation reaction and/or an oxidative coupling reaction of light alkanes In an embodiment, the installation comprises a separation unit and further comprises at least a recycle line to recycle the unconverted carbon dioxide and the unconverted hydrogen sulphide separated in the separation unit into the $CO_2$ sulphuration unit.

For example, the one or more conversion reactors are fixed bed reactors.

Advantageously, at least one fluidized bed reactor is devoid of heating means. For example, at least one fluidized bed reactor is devoid of heating means located around or inside the reactor vessel. For example, all the fluidized bed reactors are devoid of heating means. When stating that at least one of the fluidized bed reactors is devoid of "heating means", it refers to "classical' heating means, such as ovens, gas burners, hot plates and the like. There are no other heating means than the at least two electrodes of the fluidized bed reactor itself. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

In a preferred embodiment, the at least one fluidized bed reactor comprising at least two electrodes and a bed comprising particles is devoid of structured packing such as honeycomb monoliths or crossed plate.

For example, the fluidizing gas is one or more diluent gases.

For example, the at least one reactor vessel has an inner diameter of at least 100 cm, preferably at least 200 cm, more preferably at least 300 cm.

With preference, the reactor vessel comprises a reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ).

With preference, one of the electrodes is the reactor vessel or the gas distributor and/or said at least two electrodes are made in stainless steel material or nickel-chromium alloys or nickel-chromium-iron alloys.

For example, the at least one fluidized bed reactor comprises a heating zone and a reaction zone, one or more fluid nozzles to provide a stream of light alkane-comprising feedstock to the reaction zone, and optional means to transport the particles of the bed from the reaction zone back to the heating zone.

For example, the installation comprises an electrified fluidized bed unit with at least two fluidized bed reactors connected one to each other wherein at least one reactor of said at least two fluidized bed reactors is the heating zone and at least another reactor of said at least two fluidized bed reactors is the reaction zone. With preference, the electrified fluidized bed unit comprises one or more fluid nozzles arranged to inject a stream of light alkane-comprising feedstock to the at least one fluidized bed reactor being the reaction zone, means to transport the particles of the bed from the heating zone to the reaction zone when necessary and optional means to transport the particles from the reaction zone back to the heating zone. This configuration is remarkable in that a given particle bed is common to at least two fluidized bed reactors.

For example, the at least one fluidized bed reactor is a single fluidized bed reactor wherein the heating zone is the bottom part of the fluidized bed reactor while the reaction zone is the top part of the fluidised bed reactor. With preference, the installation comprises one or more fluid nozzles to inject a light alkane-comprising feedstock between the two zones. The diameter of the heating zone and reaction zone can be different to accomplish optimum conditions for heating in the bottom zone and optimum conditions for methane conversion in the top zone. Particles can move from the heating zone to the reaction zone by entrainment and the other way around from the reaction zone back to the heating zone by gravity. Optionally, particles can be collected from the upper heating zone and transferred by a separate transfer line back to the bottom heating zone.

For example, the at least one fluidized bed comprises at least two lateral zones being an outer zone and an inner zone wherein the outer zone is surrounding the inner zone, with the outer zone being the heating zone and the inner zone being the reaction zone. In a less preferred configuration, the outer zone is the reaction zone and the inner zone is the heating zone. With preference, the installation comprises one or more fluid nozzles to inject a light alkane-comprising feedstock in the reaction zone.

According to a third aspect, the disclosure provides the use of a bed comprising particles in at least one fluidized bed reactor to perform an alkane transformation into olefin according to the first aspect, the use is remarkable in that at least 10 wt. % of the particles of the bed based on the total weight of the particles of the bed are electrically conductive, have a resistivity ranging from 0.001 Ohm·cm to 500 Ohm·cm at a temperature of 800° C.

For example, the electrically conductive particles are or comprise one or more selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

For example, the electrically conductive particles are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphides being doped with one or more lower-valent cations, and any mixture thereof.

For example, the use comprises heating the bed comprising particles to a temperature ranging from 600° C. to 1500° C. in a first reactor, transporting the heated particle bed from the first reactor to a second reactor and providing a light alkane-comprising feedstock to the second reactor; with preference, at least the second reactor is a fluidized bed reactor and/or at least the second reactor is devoid of heating means; more preferably, the first reactor and the second reactor are fluidized bed reactors and/or the first and the second reactor are devoid of heating means. For example, the second reactor is devoid of electrodes.

According to a fourth aspect, the disclosure provides the use of an installation comprising at least one fluidized bed reactor to perform an alkane partial oxidation and/or oxidative coupling, remarkable in that the installation is according to the second aspect. With preference, the use of an installation of at least one fluidized bed reactor to perform an alkane partial oxidation and/or oxidative coupling in a process according to the first aspect.

The particular features, structures, characteristics or embodiments may be combined in any suitable manner, as would be apparent to a person skilled in the art from this disclosure, in one or more embodiments.

DETAILED DESCRIPTION

Figure 1:
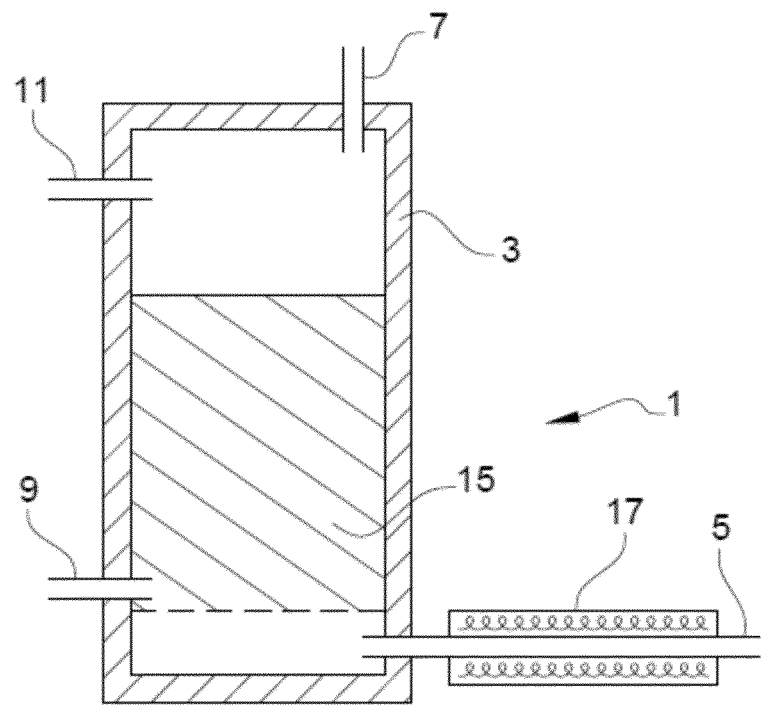
FIG. 1 illustrates an installation according to the prior art.

For the disclosure, the following definitions are given:

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The term "transition metal" refers to an element whose atom has a partially filled d sub-shell, or which can give rise to cations with an incomplete d sub-shell (IUPAC definition). According to this definition, the transition metals are Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, Db, Sg, Bh, Hs, Mt, Ds, Rg, and Cn. The metals Ga, In, Sn, Tl, Pb and Bi are considered as "post-transition" metals. The present disclosure provides a process to perform an alkane partial oxidation and/or oxidative coupling of light alkanes, said process comprising the steps of:

a) providing a stream of light alkane-comprising feedstock wherein the stream of light alkane-comprising feedstock further comprises one or more oxidants selected from carbon dioxide, carbonyl sulphide and any mixture thereof; and further providing at least one fluidized bed reactor comprising at least two electrodes and a bed comprising particles;

b) putting the particles of the bed in a fluidized state to obtain a fluidized bed, for example by passing upwardly through the said bed a gaseous stream;

c) heating the fluidized bed to a temperature ranging from 600° C. to 1500° C. to conduct the alkane transformation into olefin on the light alkane-comprising feedstock; and d) optionally, recovering the products of the reaction the process is remarkable in that the step c) of heating the fluidized bed is performed by passing an electric current through the fluidized bed; in that the particles of the bed comprise electrically conductive particles and optional particles of a catalytic composition; and in that, at least 10 wt. % of the particles based on the total weight of the particles of the bed are electrically conductive and have a resistivity ranging from 0.001 Ohm·cm to 500 Ohm·cm at of 800° C.

For example, the electrically conductive particles of the bed are or comprise one or more selected from one or more carbon-containing particles, one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof.

For example, the electrically conductive particles of the bed are or comprise one or more selected from graphite, carbon black, one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof.

In an embodiment, from 50 wt. % to 100 wt. % of the electrically conductive particles of the bed based on the total weight of the electrically conductive particles of the bed are one or more selected from graphite, carbon black, one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, in step b) the particles of the bed are put in a fluidized state by passing upwardly through the said bed a fluidizing stream being a gaseous stream comprising a light alkane-containing feedstock. For example, in step b) the particles of the bed are put in a fluidized state by passing upwardly through the said bed a fluidizing stream being a gaseous stream comprising methane. For example, the light alkane-containing feedstock is a methane feedstock. For example, the step of heating the fluidized bed is performed by passing an electric current at a voltage of at most 300 V through the fluidized bed, preferably at most 200 V, more preferably at most 150 V, even more preferably at most 120 V, most preferably at most 100 V, even most preferably at most 90 V.

The solid particulate material in the fluidized bed reactor is typically supported by a porous plate, a perforated plate, a plate with nozzles or chimneys, known as a distributor. The fluid is then forced through the distributor up and travelling through the voids between the solid particulate material. At lower fluid velocities, the solids remain settled as the fluid passes through the voids in the material, known as a packed bed reactor. As the fluid velocity is increased, the particulate solids will reach a stage where the force of the fluid on the solids is enough to counterbalance the weight of the solid particulate material. This stage is known as incipient fluidization and occurs at this minimum fluidization velocity. Once this minimum velocity is surpassed, the contents of the reactor bed begin to expand and become fluidized.

Depending on the operating conditions and properties of the solid phase various flow regimes can be observed in such reactors. The minimum fluidization velocity needed to achieve bed expansion depends upon the size, shape, porosity and density of the particles and the density and viscosity of the upflowing fluid.

P. R. Gunjal, V. V. Ranade, in Industrial Catalytic Processes for Fine and Specialty Chemicals, (2016) reads that four different categories of fluidization based on the mean particle have been differentiated by Geldart that determine the fluidization regimes:

type A, aeratable fluidization (medium size, medium-density particles which are easier to fluidize; Particles of typically 30-100 μm, density~1500 kg/m$^3$);

type B, sand-like fluidization (heavier particles which are difficult to fluidize; Particles of typically 100-800 μm, density between 1500 and 4000 kg/m$^3$);

type C, cohesive fluidization (typical powder-like solid particle fluidization; Fine-size particles (~20 μm) with a dominance of intraparticle or cohesive forces); and type D, spoutable fluidization (large density and larger particle~1-4 mm, dense and spoutable).

Fluidization may be broadly classified into two regimes (Fluid Bed Technology in Materials Processing, 1999 by CRC Press): homogeneous fluidization and heterogeneous fluidization. In homogeneous or particulate fluidization, particles are fluidized uniformly without any distinct voids. In heterogeneous or bubbling fluidization, gas bubbles devoid of solids are distinctly observable. These voids behave like bubbles in gas-liquid flows and exchange gas with the surrounding homogeneous medium with a change in size and shape while rising in the medium. In particulate fluidization, the bed expands smoothly with substantial particle movement and the bed surface is well defined. Particulate fluidization is observed only for Geldart-A type particles. A bubbling fluidization regime is observed at much higher velocities than homogeneous fluidization, in which distinguishable gas bubbles grow from the distributor, may coalesce with other bubbles and eventually burst at the surface of the bed. These bubbles intensify the mixing of solids and gases and bubble sizes tend to increase further with a rise in fluidization velocity. A slugging regime is observed when the bubble diameter increases up to the reactor diameter. In a turbulent regime, bubbles grow and start breaking up with the expansion of the bed. Under these conditions, the top surface of the bed is no longer distinguishable. In fast fluidization or pneumatic fluidization, particles are transported out of the bed and need to be recycled back into the reactor. No distinct bed surface is observed.

Fluidized bed reactors have the following advantages:

Uniform Particle Mixing: Due to the intrinsic fluid-like behaviour of the solid particulate material, fluidized beds do not experience poor mixing as in packed beds. The elimination of radial and axial concentration gradients also allows for better fluid-solid contact, which is essential for reaction efficiency and quality.

Uniform Temperature Gradients: Many chemical reactions require the addition or removal of heat. Local hot or cold spots within the reaction bed are avoided in a fluidized situation.

Ability to Operate the Reactor Continuously: The fluidized bed nature of these reactors allows for the ability to continuously withdraw products and introduce new reactants into the reaction vessel. On top of continuous operation of the chemical reactions, the fluidized bed allows also to continuously or at a given frequency withdraw solid material or add continuously or at a given frequency new fresh solid material thanks to the flowable solid particulate material. Heat can be produced by passing an electrical current through a conducting material that has sufficiently high resistivity (the resistor) to transform electricity into heat. Electrical resistivity (also called specific electrical resistance or volume resistivity, is an intrinsic property independent of shape and size) and its inverse, electrical conductivity, is a fundamental property of a material that quantifies how strongly it resists or conducts electric current (SI unit of electrical resistivity is the ohm-meter ($\Omega \cdot m$) and for conductivity Siemens per meter (S/m)).

When electricity is passed through a fixed bed of electrically conducting particulate solids, having a sufficient resistivity, the bed offers resistance to the flow of current; this resistance depends on many parameters, including the nature of the solid, the nature of the linkages among the particles within the bed, the bed voidage, the bed height, the electrode geometry, etc. If the same fixed bed is fluidized by passing gas, the resistance of the bed increases; the resistance offered by the conducting particles generates heat within the bed and can maintain the bed in isothermal conditions (termed an electrothermal fluidized bed or electrofluid reactor). In many high-temperature reactions, electrofluid reactors offer in situ heating during the reaction and are particularly useful for operating endothermic reactions and hence save energy because no external heating or transfer of heat is required. It is a prerequisite that at least part of the solid particulate material is electrically conducting but non-conducting solid particulates can be mixed and still result in enough heat generation. Such non-conducting or very high resistivity solids can play a catalytic role in the chemical conversion. The characteristics of the bed material determine the resistance of an electrothermal fluidized bed furnace; as this is a charge resistor type of heat generation, the specific resistivity of the particles affects the bed resistance. The size, shape, composition, and size distribution of the particles also influence the magnitude of the bed resistance. Also, when the bed is fluidized, the voids generated between the particles increases the bed resistance. The total resistance of the bed is the sum of two components, e.g., the electrode contact-resistance (i.e., the resistance between the electrode and the bed) and the bed resistance. A large contact-resistance will cause extensive local heating in the vicinity of the electrode while the rest of the bed stays rather cool. The following factors determine the contact-resistance: current density, fluidization velocity, type of bed material, electrode size and the type of material used for the electrodes. The electrode compositions can be advantageously metallic like iron, cast iron or other steel alloys, copper or a copper-based alloy, nickel or a nickel-based alloy or refractory like metal, intermetallics or an alloy of Zr, Hf, V, Nb, Ta, Cr, Mo, W or ceramic-like carbides, nitrides or carbon-based like graphite. The area of contact between the bed material and the electrodes can be adjusted, depending on the electrode submergence and the amount of particulate material in the fluidized bed. Hence, the electrical resistance and the power level can be manipulated by adjusting these variables. Advantageously, to prevent overheating of the electrodes compared to the fluidised bed, the resistivity of the electrode should be lower (and hence the joule heating) than of the particulate material of the fluidized bed. In a preferred embodiment, the electrodes can be cooled by passing a colder fluid inside or outside the electrodes. Such fluids can be any liquid that vaporises upon a heating, gas stream or can be a part of the colder feedstock that first cools the electrode before entering the fluidised bed.

Bed resistance can be predicted by the ohmic law. The mechanism of current transfer in fluidized beds is believed to occur through current flow along continuous chains of conducting particles at low operating voltages. At high voltages, a current transfer occurs through a combination of chains of conducting particles and arcing between the electrode and the bed as well as particle-to-particle arcing that might ionize the gas, thereby bringing down the bed resistance. Arcing inside the bed, in principle, is not desirable as it would lower the electrical and thermal efficiency. The gas velocity impacts strongly the bed resistance, a sharp increase in resistance from the settled bed onward when the gas flow rate is increased; a maximum occurred close to the incipient fluidization velocity, followed by a decrease at higher velocities. At gas flow rates sufficient to initiate slugging, the resistance again increased. Average particle size and shape impact resistance as they influence the contacts points between particles. In general, the bed resistivity increases 2 to 5 times from a settled bed (e.g. 20 Ohm·cm for graphite) to the incipient fluidisation (60 Ohm·cm for graphite) and 10 to 40 times from a settled bed to twice (300 Ohm·cm for graphite) the incipient fluidisation velocity. Non or less-conducting particles can be added to conducting particles. If the conducting solid fraction is small, the resistivity of the bed would increase due to the breaking of the linkages in the chain of conducting solids between the electrodes. If the non-conducting solid fraction is finer in size, it would fill up the interstitial gaps or voidage of the larger conducting solids and hence increase the resistance of the bed.

In general, for a desired high heating power, a high current at a low voltage is preferred. The power source can be either AC or DC. Voltages applied in an electrothermal fluidized bed are typically below 100 V to reach enough heating power. The electrothermal fluidized bed can be controlled in the following three ways:

1. Adjusting the gas flow: Because the conductivity of the bed depends on the extent of voidage or gas bubbles inside the bed, any variation in the gas flow rate would change the power level; hence the temperature can be controlled by adjusting the fluidizing gas flow rate. The flow rate required for optimum performance corresponds to a velocity which equals or slightly exceeds the minimum fluidization velocity.
2. Adjusting the electrode submergence: The power level can also be controlled by varying the electrode immersion level inside the bed because the conductivity of the bed is dependent on the area of contact between the conducting particles and the electrode: the surface area of the electrode available for current flow increases with electrode submergence, leading to a reduction in overall resistance.

3. Adjusting the applied voltage: although changing the power level by using the first two methods is often more affordable or economical than increasing the applied voltage, however in electrothermal fluidized beds three variables are available to control the produced heating power.

The wall of the reactor is generally made of graphite, ceramics (like SiC), high-melting metals or alloys as it is versatile and compatible with many high-temperature reactions of industrial interest. The atmosphere for the reaction is often restricted to the neutral or the reducing type as an oxidising atmosphere can combust carbon materials or create a non-conducting metal oxide layer on top of metals or alloys. The wall and/or the distribution plate itself can act as an electrode for the reactor. The fluidized solids can be graphite or any other high-melting-point, electrically conducting particles. The other electrodes, which is usually immersed in the bed, can also be graphite or a high-melting-point metal, intermetallics or alloys.

It may be advantageous to generate the required reaction heat by heating the conductive particles and/or catalyst particles in a separate zone of the reactor where little or substantially no feedstock hydrocarbons are present, but only diluent gases. The benefit is that the appropriate conditions of fluidization to generate heat by passing an electrical current through a bed of conductive particles can be optimized whereas the optimal reaction conditions during hydrocarbon transformation can be selected for the other zone of the reactor. Such conditions of optimal void fraction and linear velocity might be different for heating purposes and chemical transformation purposes.

In an embodiment of the present disclosure, the installation comprises of two zones arranged in series namely a first zone being a heating zone and a second zone being a reaction zone, where the conductive particles and catalyst particles are continuously moved or transported from the first zone to the second zone and vice versa. The first and second zones can be different parts of a fluidized bed or can be located in separate fluidized beds reactors connected one to each other.

In the said embodiment, the process to perform the alkane transformation into olefin comprises the steps of:
a) providing a stream of a light alkane-comprising feedstock comprising one or more alkanes and one or more oxidants selected from carbon dioxide, carbonyl sulphide and any mixture thereof; and further providing at least one fluidized bed reactor comprising at least two electrodes and a bed comprising particles;
b) putting the particles in a fluidized state, to obtain a fluidized bed;
c) heating the fluidized bed to a temperature ranging from 600° C. to 1500° C. to conduct the alkane partial oxidation and/or the oxidative coupling reaction of light alkanes on the light alkane-comprising feedstock; and
d) optionally, recovering the products of the reaction;
wherein the step c) of heating the fluidized bed is performed by passing an electric current through the fluidized bed; wherein the particles of the bed comprise electrically conductive particles and optional particles of a catalytic composition; and wherein at least 10 wt. % of the particles based on the total weight of the particles of the bed are electrically conductive particles, have a resistivity ranging from 0.001 Ohm·cm to 500 Ohm·cm at 800° C.; wherein the at least one fluidized bed reactor provided in step a) comprises a heating zone and a reaction zone and wherein the step c) of heating the fluidized bed to a temperature ranging from 600° C. to 1500° C. to conduct the alkane transformation into olefin on the light alkane-comprising feedstock comprises the following sub-steps:
heating the fluidized bed to a temperature ranging from 600° C. to 1500° C. by passing an electric current through the heating zone of the at least one fluidized bed,
transporting the heated particles from the heating zone to the reaction zone,
in the reaction zone, putting the heated particles in a fluidized state by passing upwardly through the said bed of the reaction zone a stream comprising a light alkane-comprising feedstock and optional diluent gases to obtain a fluidized bed and to conduct the endothermic alkane partial oxidation reaction and/or oxidative coupling reaction on the light alkane-comprising feedstock,
optionally, recovering the particles from the reaction zone and recycling them to the heating zone.

For example, the electrically conductive particles are or comprise one or more selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and/or any mixture thereof.

For example, the electrically conductive particles are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphides being doped with one or more lower-valent cations, and/or any mixture thereof.

For example, the stream of light alkane feedstock is devoid of diluent.

For example, the stream of light alkane feedstock is enriched with one or more oxidants by in situ mixing in the reaction zone.

For example, the at least one fluidized bed reactor is at least two fluidized bed reactors connected one to each other wherein at least one of said at least two fluidized bed reactors is the heating zone and at least another of said at least two fluidized bed reactors is the reaction zone. With preference, the at least one fluidized bed reactor being the heating zone comprises gravitational or pneumatic transport means to transport the particles from the heating zone to the reaction zone and/or the installation comprises means arranged to inject a light alkane-comprising feedstock to the at least one fluidized bed reactor being the reaction zone. The installation is devoid of means to inject a light alkane-comprising feedstock to the at least one fluidized bed reactor being the heating zone.

For example, the at least one fluidized bed reactor is a single fluidized bed reactor wherein the heating zone is the bottom part of the fluidized bed reactor while the reaction zone is the top part of the fluidised bed reactor. With preference, the installation comprises means to inject a light alkane-comprising feedstock and/or diluent between the two zones. The diameter of the heating zone and reaction zone can be different to accomplish optimum conditions for heating in the bottom zone and optimum conditions for hydrocarbon conversion in the top zone. Particles can move from the heating zone to the reaction zone by entrainment and the other way around from the reaction zone back to the heating zone by gravity. Optionally, particles can be collected from the upper heating zone and transferred by a separate transfer line back to the bottom heating zone.

It is understood that the light alkane-comprising feedstock is provided to the reaction zone and that when the heating zone is separated from the reaction zone then, with preference, no light alkane-comprising feedstock is provided to the heating zone. When the heating zone and the reaction zone are mixed (i.e. the same zone); the stream provided in step b) comprises a light alkane-comprising feedstock.

In an embodiment, step a) comprise a sub-step of production of a COS-containing stream, wherein said sub-step comprise providing feedstream containing at least 30 wt. % of carbon dioxide ($CO_2$) and at least 20 wt. % of hydrogen sulphide ($H_2S$) based on the total weight of said feedstream and converting said feedstream into a COS-containing stream; wherein the conversion is performed at a temperature ranging from 50 to 800° C., at a pressure ranging from 0.01 to 5 MPa (from 0.1 to 50 bar) and at a GHSV ranging from 0.1 to 10 $h^{-1}$ wherein the COS-containing stream is containing water and at least 10 wt. % of carbonyl sulphide (COS) based on the total weight of said COS-containing stream.

The conversion can be described with the following chemical equation:

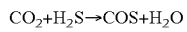

$$CO_2 + H_2S \rightarrow COS + H_2O$$

The reaction will be carried out letting the gaseous carbon dioxide and gaseous hydrogen sulphide react together at a temperature ranging from 50 to 800° C. at a pressure ranging from 0.1 to 5 MPa (1 to 50 bar) and at a GHSV ranging from 0.1 to 10 $h^{-1}$.

The conversion reaction produces water. It is preferable to remove the water to avoid having the COS hydrolyzed into $CO_2$ and $H_2S$. Removal of water also helps to push the equilibrium of the reaction to produce more carbonyl sulphide. Water can be removed in a separated substep of drying for instance with a sorbent. Water can also be separated at least partially during the sub-step of production of a COS-containing stream using a sorbent. The sorbent used in the sub-steps of production of a COS-containing stream and of drying of the COS-containing stream can be the same or different.

In an embodiment, the sub-step of production of a COS-containing stream is performed in a separate reactor being a conversion that preferably contains a sorbent.

Any suitable sorbents capable of adsorbing water can be used. Silica, silica gel, or molecular sieves such as 13X or any mixture thereof can for instance be used to dry the feedstream. Once saturated, the sorbents can be regenerated by any methods known in the art. For instance, the sorbents can be put offline and the pressure and/or the temperature can be changed to desorb the water and to regenerate the sorbents. A dry gas such as $N_2$ can also be used to desorb the water from the sorbent. In one embodiment, two or more trains of conversion reactors are used as swing beds. In that case, one bed of sorbent (first bed) is used in the conversion reactor until it has been saturated, at which point it is replaced by another bed (second bed) of sorbent in the conversion reactor, while the first bed is dried to remove the water. In another embodiment, the sorbent may be removed and sent and to a regenerator to be dried, and then recycled for use again In an embodiment, the sub-step of production of a COS-containing stream is performed in presence of a COS-conversion catalyst.

In a preferred embodiment, the sub-step of production of a COS-containing stream is performed in a fixed bed conversion reactor preferably using a sulphide catalyst being preferably a catalyst that comprises at least one metal of group VI, B for example Mo, W in combination or not with a promotor selected from at least one metal of group VIII and/VIIIB, for example, Ni and/or Co, and/or a mixture thereof, these metals being used in the sulfided form and preferably supported on alumina, titania, zirconia, silica, carbon and/or mixtures thereof.

In a preferred embodiment, the COS-conversion catalyst is mixed metal sulphides, and sulphides of transition metals, in particular silica-supported metal sulphides. Other suitable catalysts include silica, amorphous silica-alumina (ASA) commercially available from CRI, and zeolite catalysts such as ZSM-5 commercially available from Zeolyst International. When the catalyst is a sulphur based catalyst, it is preferably based on metal oxides chosen from oxides of metals from Group VI-B (Mo, W, and the like) and VIII-B (Co, Ni, Pt, Pd, Ru, Rh, and the like) supported on a support chosen from alumina, silica/alumina, zeolite, ferrierite, phosphated alumina, phosphated silica/alumina, and the like. Preferably, the COS-conversion catalyst used will be NiMo, CoMo, NiW, PtPd or a mixture of two or more of these. The COS-conversion catalyst used can also be based on metals in the bulk state, such as the commercially known catalyst of Nebula type. The COS-conversion catalyst can also be based on metal oxides chosen from oxides of metals from Group VI-B (Mo, W, and the like) and VIII-B (Co, Ni, Pt, Pd, Ru, Rh, and the like) supported on a support chosen from alumina, silica/alumina, zeolite, ferrierite, phosphated alumina, phosphated silica/alumina, and the like, preferably NiMo, CoMo, NiW, PtPd or a mixture of two or more of these.

Even more preferably, the COS-conversion catalyst is based on nickel oxides on acidic support, such as amorphous silica/alumina, zeolite, ferrierite, phosphated alumina, phosphated silica/alumina, and the like.

The COS-conversion catalyst can be used alone or can be mixed with a sorbent being preferably chosen among silica, silica gel, or molecular sieves such as 13X or any mixture thereof. In a more preferred embodiment, the COS-conversion catalyst presents a sorption function. For instance, the active phase of the COS-conversion catalyst can be deposited on a support being capable to adsorb water. Non-limiting examples of possible supports for the COS-conversion catalyst include silica, silica gel, or molecular sieves such as 13X or any mixture thereof.

In a preferred embodiment, the COS-containing stream contains at least 15 wt. % of carbonyl sulphide (COS) based on the total weight of the COS-containing stream; preferably at least 20 wt. % of carbonyl sulphide (COS) to at most 80 wt. % preferably at most 75 wt. %. To increase the content of COS in the COS-containing stream, the person skilled in the art may add a sub-step of separating water from the COS-containing stream and preferably separating the unconverted carbon dioxide ($CO_2$) and the unconverted hydrogen sulphide ($H_2S$) if any. In a preferred embodiment, the unconverted carbon dioxide ($CO_2$) and the unconverted hydrogen sulphide ($H_2S$) recovered are recycled at the inlet of the conversion reactor.

In a preferred embodiment, the feedstream is selected to comprise at least 20 wt. % of carbon dioxide ($CO_2$) based on the total weight of said feedstream.

In a preferred embodiment, the feedstream is selected to comprise at least 20 wt. % of hydrogen sulphide ($H_2S$) based on the total weight of said feedstream.

In a preferred embodiment, the feedstream is selected to comprise at most 10 wt. % of water, more preferably at most 5 wt. % of water, even more preferably at most 1 wt. % of water, in the most preferred embodiment, the feedstream does not comprise water. When the feedstream comprises water, it is preferably removed with the help of a sorbent.

The Bed Comprising Particles

To achieve the required temperature necessary to carry out the alkane partial oxidation reaction and/or oxidative coupling reaction, at least 10 wt. % of the particles based on the total weight of the particles of the bed are electrically conductive, have a resistivity ranging from 0.001 Ohm·cm to 500 Ohm·cm at 800° C.

For example, the electrically particles of the bed are or comprise one or more selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

For example, the electrically particles of the bed are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphides being doped with one or more lower-valent cations, and any mixture thereof.

For example, from 50 wt. % to 100 wt. % of the electrically conductive particles of the bed based on the total weight of the electrically conductive particles of the bed are one or more selected from graphite, carbon black, one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

In an embodiment, from 50 wt. % to 100 wt. % of the electrically conductive particles of the bed based on the total weight of the electrically conductive particles of the bed are devoid of graphite and/or carbon black; preferably, from 60 wt. % to 95 wt. %; more preferably from 70 wt. % to 90 wt. %; and even more preferably from 75 wt. % to 85 wt. %.

For example, the content of electrically conductive particles is ranging from 10 wt. % to 100 wt. % based on the total weight of the particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the content of electrically conductive particles based on the total weight of the bed is at least 12 wt. % based on the total weight of the particles of the bed; preferably, at least 15 wt. %, more preferably, at least 20 wt. %; even more preferably at least 25 wt. %, and most preferably at least 30 wt. % or at least 40 wt. % or at least 50 wt. % or at least 60 wt. %.

For example, the electrically conductive particles have a resistivity ranging from 0.005 to 400 Ohm·cm at 800° C., preferably ranging from 0.01 to 300 Ohm·cm at 800° C.; more preferably ranging from 0.05 to 150 Ohm·cm at 800° C. and most preferably ranging from 0.1 to 100 Ohm·cm at 800° C.

For example, the electrically conductive particles have a resistivity of at least 0.005 Ohm·cm at 800° C.; preferably of at least 0.01 Ohm·cm at 800° C., more preferably of at least 0.05 Ohm·cm at 800° C.; even more preferably of at least 0.1 Ohm·cm at 800° C., and most preferably of at least 0.5 Ohm·cm at 800° C.

For example, the electrically conductive particles have a resistivity of at most 400 Ohm·cm at 800° C.; preferably of at most 300 Ohm·cm at 800° C., more preferably of at most 200 Ohm·cm at 800° C.; even more preferably of at most 150 Ohm·cm at 800° C., and most preferably of at most 100 Ohm·cm at 800° C.

For example, the particles of the bed have an average particle size ranging from 5 to 300 µm as determined by sieving according to ASTM D4513-11, preferably ranging from 10 to 200 µm and more preferably ranging from 30 to 150 µm.

For example, the electrically conductive particles of the bed have an average particle size ranging from 5 to 300 µm as determined by sieving according to ASTM D4513-11, preferably ranging from 10 to 200 µm and more preferably ranging from 30 to 150 µm.

The electrical resistance is measured by a four-probe DC method using an ohmmeter. A densified power sample is shaped in a cylindrical pellet that is placed between the probe electrodes. Resistivity is determined from the measured resistance value, R, by applying the known expression $\rho = R \times A/L$, where L is the distance between the probe electrodes typically a few millimetres and A the electrode area.

The electrically conductive particles of the bed can exhibit electronic, ionic or mixed electronic-ionic conductivity. The ionic bonding of many refractory compounds allows for ionic diffusion and correspondingly, under the influence of an electric field and appropriate temperature conditions, ionic conduction.

The electrical conductivity, $\sigma$, the proportionality constant between the current density j and the electric field E, is given by $$\sigma = j/E = \Sigma c_i \times Z_i q \times \mu_i$$

where $c_i$ is the carrier density (number/$cm^3$), $\mu_i$ the mobility ($cm^2$/Vs), and $Z^i q$ the charge ($q = 1.6 \times 10^{-19}$ C) of the ith charge carrier. The many orders of magnitude differences in $\sigma$ between metals, semiconductors and insulators generally result from differences in c rather than µ. On the other hand, the higher conductivities of electronic versus ionic conductors are generally due to the much higher mobilities of electronic versus ionic species.

The most common materials that can be used for resistive heating is subdivided into nine groups:
(1) Metallic alloys for temperatures up to 1200-1400° C.,
(2) non-metallic resistors like silicon carbide (SiC), molybdenum disilicide ($MoSi_2$), nickel silicide (NiSi), sodium silicide ($Na_2Si$), magnesium silicide ($Mg_2Si$), platinum silicide (PtSi), titanium silicide (TiSi$_2$) and tungsten silicide (WSi$_2$) up to 1600-1900° C.,
(3) several mixed oxides and/or mixed sulphides being doped with one or more lower-valent cations with variable temperature optima,
(4) graphite up to 2000° C.,
(5) metallic carbides,
(6) transition metal nitrides,
(7) metallic phosphides,
(8) superionic conductors, and
(9) phosphate electrolytes.

A first group of metallic alloys, for temperatures up to 1150-1250° C., can be constituted by Ni—Cr alloys with low Fe content (0.5-2.0%), preferably alloy Ni—Cr (80% Ni, 20% Cr) and (70% Ni, 30% Cr). Increasing the content of Cr increases the material resistance to oxidation at high temperatures. A second group of metallic alloys having three components are Fe—Ni—Cr alloys, with maximum operating temperature in an oxidizing atmosphere to 1050-1150° C. but which can be conveniently used in reducing atmospheres or Fe—Cr—Al (chemical composition 15-30% Cr, 2-6% Al and Fe balance) protecting against corrosion by a surface layer of oxides of Cr and Al, in oxidizing atmospheres can be used up to 1300-1400° C. Silicon carbide as non-metallic resistor can exhibit wide ranges of resistivity that can be controlled by the way they are synthesized and the presence of impurities like aluminium, iron, oxide, nitrogen or extra carbon or silicon resulting in non-stoichiometric silicon carbide. In general silicon carbide has a high resistivity at low temperature but has good resistivity in the range of 500 to 1200° C. In an alternative embodiment, the non-metallic resistor can be devoid of silicon carbide, and/or can comprise molybdenum disilicide (MoSi$_2$), nickel silicide (NiSi), sodium silicide (Na$_2$Si), magnesium silicide (Mg$_2$Si), platinum silicide (PtSi), titanium silicide (TiSi$_2$), tungsten silicide (WSi$_2$) or a mixture thereof.

Graphite has rather low resistivity values, with a negative temperature coefficient up to about 600° C. after which the resistivity starts to increase.

Many mixed oxides and/or mixed sulphides being doped with one or more lower-valent cations, having in general too high resistivity at low temperature, become ionic or mixed conductors at high temperature. The following circumstances can make oxides or sulphides sufficient conductors for heating purposes: ionic conduction in solids is described in terms of the creation and motion of atomic defects, notably vacancies and interstitials of which its creation and mobility is very positively dependent on temperature. Such mixed oxides or sulphides are ionic or mixed conductors, namely being doped with one or more lower-valent cations. Three mechanisms for ionic defect formation in oxides are known: (1) Thermally induced intrinsic ionic disorder (such as Schottky and Frenkel defect pairs resulting in non-stoichiometry), (2). Redox-induced defects and (3) Impurity-induced defects. The first two categories of defects are predicted from statistical thermodynamics and the latter form to satisfy electroneutrality. In the latter case, high charge carrier densities can be induced by substituting lower valent cations for the host cations. Mixed oxides and/or mixed sulphides with fluorite, pyrochlore or perovskite structure are very suitable for substitution by one or more lower-valent cations.

Several sublattice disordered oxides or sulphides have high ion transport ability at increasing temperature. These are superionic conductors, such as LiAlSiO$_4$, Li$_{10}$GeP$_2$S$_{12}$, Li$_{3.6}$Si$_{0.6}$P$_{0.4}$O$_4$, NaSICON (sodium (Na) Super Ionic CONductor) with the general formula Na$_{1+x}$Zr$_2$P$_{3-x}$Si$_x$O$_{12}$ with $0<x<3$, for example Na$_3$Zr$_2$PSi$_2$O$_{12}$ (x=2), or sodium beta alumina, such as NaAl$_{11}$O$_{17}$, Na$_{1.6}$Al$_{11}$O$_{17.3}$, and/or Na$_{1.76}$Li$_{0.38}$Al$_{10.62}$O$_{17}$.

High concentrations of ionic carriers can be induced in intrinsically insulating solids and creating high defective solids. Thus, the electrically conductive particles of the bed are or comprise one or more mixed oxides being ionic or mixed conductor, namely being doped with one or more lower-valent cations, and/or one or more mixed sulphides being ionic or mixed conductor, namely being doped with one or more lower-valent cations. With preference, the mixed oxides are selected from one or more oxides having a cubic fluorite structure being at least partially substituted with one or more lower-valent cations, preferentially selected from Sm, Gd, Y, Sc, Yb, Mg, Ca, La, Dy, Er, Eu; and/or from one or more ABO$_3$-perovskites with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or from one or more ABO$_3$-perovskites with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more A$_2$B$_2$O$_7$-pyrochlores with A trivalent cation and B tetra-valent cation being at least partially substituted in A position with one or more lower-valent cations, preferentially selected from Ca or Mg, and comprising at least one of Sn, Zr and Ti in B position.

With preference, the one or more mixed sulphides are selected from one or more sulphides having a cubic fluorite structure being at least partially substituted with one or more lower-valent cations, preferentially selected from Sm, Gd, Y, Sc, Yb, Mg, Ca, La, Dy, Er, Eu; and/or from one or more ABS$_3$ structures with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or from one or more ABS$_3$ structures with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more A$_2$B$_2$S$_7$ structures with A trivalent cation and B tetra-valent cation being at least partially substituted in A position with one or more lower-valent cations, preferentially selected from Ca or Mg, and comprising at least one of Sn, Zr and Ti in B position.

With preference, the degree of substitution in the one or more mixed oxides doped with one or more lower-valent cations and having a cubic fluorite structure is between 1 and 15 atom % based on the total number of atoms present in the one or more oxides or sulphides having a cubic fluorite structure, in the one or more ABO$_3$-perovskites with A and B tri-valent cations, in the one or more ABO$_3$-perovskites with A bivalent cation and B tetra-valent cation or in the one or more A$_2$B$_2$O$_7$-pyrochlores with A trivalent cation and B tetra-valent cation respectively, preferably between 3 and 12 atom %, more preferably between 5 and 10 atom %.

With preference, the degree of substitution in the one or more mixed oxides doped with one or more lower-valent cations is between 1 and 50 atom % based on the total number of atoms present in the one or more ABO$_3$-perovskites with A and B tri-valent cations, in the one or more $ABO_3$-perovskites with A bivalent cation and B tetra-valent cation or in the one or more $A_2B_2O_7$-pyrochlores with A trivalent cation and B tetra-valent cation respectively, preferably between 3 and 20 atom %, more preferably between 5 and 15 atom %.

With preference, the degree of substitution in the one or more mixed sulphides doped with one or more lower-valent cations and having a cubic fluorite structure is between 1 and 15 atom % based on the total number of atoms present in the one or more $ABS_3$ structures with A and B tri-valent cations, in the one or more $ABS_3$ structures with A bivalent cation and B tetra-valent cation or in the one or more $A_2B_2S_7$ structures with A trivalent cation and B tetra-valent cation respectively, preferably between 3 and 12 atom %, more preferably between 5 and 10 atom %.

With preference, the degree of substitution in the one or more mixed sulphides doped with one or more lower-valent cations is between 1 and 50 atom % based on the total number of atoms present in the one or more $ABS_3$ structures with A and B tri-valent cations, in the one or more $ABS_3$ structures with A bivalent cation and B tetra-valent cation or in the one or more $A_2B_2S_7$ structures with A trivalent cation and B tetra-valent cation respectively, preferably between 3 and 20 atom %, more preferably between 5 and 15 atom %.

Said one or more oxides having a cubic fluorite structure, said one or more $ABO_3$-perovskites with A and B tri-valent cations, said one or more $ABO_3$-perovskites with A bivalent cation and B tetra-valent cation or said one or more $A_2B_2O_7$-pyrochlores with A trivalent cation and B tetra-valent cation being at least partially substituted with lower valent cations, said one or more sulphides having a cubic fluorite structure, said one or more $ABS_3$ structures with A and B tri-valent cations, said one or more $ABS_3$ structures with A bivalent cation and B tetra-valent cation, said one or more $A_2B_2S_7$ structures with A trivalent cation and B tetra-valent cation being at least partially substituted with lower-valent cations also means that the same element, being a high-valent cation, can be reduced in the lower-valent equivalent, for example, Ti(IV) can be reduced in Ti(III) and/or Co(III) can be reduced in Co(II) and/or Fe(III) can be reduced in Fe(II) and/or Cu(II) can be reduced in Cu(I).

Phosphate electrolytes such as $LiPO_4$ or $LaPO_4$ can also be used as electrically conductive particles.

Metallic carbides, transition metal nitrides and metallic phosphides can also be selected as electrically conductive particles. For example, metallic carbides are selected from iron carbide ($Fe_3C$), molybdenum carbide (such as a mixture of MoC and $Mo_2C$). For example, said one or more transition metal nitrides are selected from zirconium nitride (ZrN), tungsten nitride (such as a mixture of $W_2N$, WN, and $WN_2$), vanadium nitride (VN), tantalum nitride (TaN), and/or niobium nitride (NbN). For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

It is a preferred embodiment of the present disclosure, the electrically conductive particles that exhibit only sufficiently low resistivity at a high temperature can be heated by external means before reaching the high enough temperature where resistive heating with electricity overtakes or can be mixed with a sufficiently low resistivity solid at a low temperature so that the resulting resistivity of the mixture allows to heat the fluidized bed to the desired reaction temperature.

For example, the electrically conductive particles of the bed are or comprise silicon carbide. For example, at least 10 wt. % of the electrically conductive particles based on the total weight of the electrically conductive particles of the bed are silicon carbide particles and have a resistivity ranging from 0.001 Ohm·cm to 500 Ohm·cm at of 800° C.

In the embodiment wherein the electrically conductive particles of the bed are or comprise silicon carbide, the person skilled in the art will have the advantage to conduct a step of pre-heating with a gaseous stream said fluidized bed reactor before conducting reaction(s) in the fluidized bed reactor. Advantageously, the gaseous stream is a stream of inert gas, i.e., nitrogen, argon, helium, methane, carbon dioxide, hydrogen or steam. The temperature of the gaseous stream can be at least 500° C., or at least 550° C., or at least 600° C., or at least 650° C., or at least 700° C., or at least 750° C., or at least 800° C., or at least 850° C., or at least 900° C. Advantageously, the temperature of the gaseous stream can be comprised between 500° C. and 900° C., for example between 600° C. and 800° C. or between 650° C. and 750° C. Said gaseous stream of inert gas can also be used as the fluidification gas. The pre-heating of the said gaseous stream of inert gas is performed thanks to conventional means, including using electrical energy. The temperature of the gaseous stream used for the preheating of the bed doesn't need to reach the temperature reaction.

Indeed, the resistivity of silicon carbide at ambient temperature is high, to ease the starting of the reaction, it may be useful to heat the fluidized bed by external means, as with preference the fluidized bed reactor is devoid of heating means. Once the bed is heated at the desired temperature, the use of a hot gaseous stream may not be necessary.

However, in an embodiment, the electrically conductive particles of the bed are or comprise a mixture of silicon carbide particles and electrically conductive particles different from silicon carbide particles.

The pre-heating step may be also used in the case wherein electrically conductive particles different from silicon carbide particles are present in the bed. For example, it may be used when the content of silicon carbide in the electrically conductive particles of the bed is more than 80 wt. % based on the total weight of the particles of the bed, for example, more than 85 wt. %, for example, more than 90 wt. %, for example, more than 95 wt. %, for example, more than 98 wt. %, for example, more than 99 wt. %. However, a pre-heating step may be used whatever is the content of silicon carbide particles in the bed.

In the embodiment wherein the electrically conductive particles of the bed are or comprise a mixture of silicon carbide particles and electrically conductive particles different from silicon carbide particles, the electrically conductive particles of the bed may comprise from 10 wt. % to 99 wt. % of silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed are or comprise a mixture of silicon carbide particles and electrically conductive particles different from silicon carbide particles and the electrically conductive particles of the bed comprises at least 40 wt. % of silicon carbide particles based on the total weight of the electrically conductive particles of the bed; preferably at least 50 wt. %, more preferably at least 60 wt. %, even more preferably at least 70 wt. % and most preferably at least 80 wt. %.

In an embodiment, the electrically conductive particles of the bed may comprise from 10 wt. % to 90 wt. % of electrically conductive particles different from silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

However, it may be interesting to keep the content of electrically conductive particles different from silicon carbide particles quite low in the mixture. Thus, in an embodiment, the electrically conductive particles of the bed are or comprise a mixture of silicon carbide particles and electrically conductive particles different from silicon carbide particles and electrically conductive particles of the bed comprises from 1 wt. % to 20 wt. % of electrically conductive particles different from silicon carbide based on the total weight of the electrically conductive particles of the bed; preferably, from 2 wt. % to 15 wt. %, more preferably, from 3 wt. % to 10 wt. %, and even more preferably, from 4 wt. % to 8 wt. %.

For example, the electrically conductive particles of the bed are or comprise a mixture of silicon carbide particles and particles different from silicon carbide particles and the said particles different from silicon carbide particles are or comprise graphite particles.

Thus, in an embodiment, the electrically conductive particles are a combination of silicon carbide particles and graphite particles. Such electrically conductive particles, upon the electrification of the fluidized bed reactor, will heat up and because of their fluidification, will contribute to the raise and/or to the maintaining of the temperature within the reactor. The Joule heating of graphite allows accelerating the heating of the reactant and/or of the other particles that are present within the fluidized bed reactor.

For example, graphite can be flake graphite. It is also preferable that the graphite has an average particle size ranging from 1 to 400 µm as determined by sieving according to ASTM D4513-11, preferably from 5 to 300 µm, more preferably ranging from 10 to 200 µm and most preferably ranging from 30 to 150 µm.

The presence of graphite particles in the bed allows applying the process according to the disclosure with or without the pre-heating step, preferably without the pre-heating step. Indeed, the graphite particles, upon the electrification of the fluidized bed reactor, will heat up and because of their fluidification, will contribute to raising and/or maintaining the desired temperature within the reactor.

The Silicon Carbide Particles

For example, the silicon carbide is selected from sintered silicon carbide, nitride-bounded silicon carbide, recrystallised silicon carbide, reaction bonded silicon carbide and any mixture thereof.

Sintered SiC (SSiC) is a self-bonded material containing a sintering aid (typically boron) of less than 1% by weight.

Recrystallized silicon carbide (RSiC), a high purity SiC material sintered by the process of evaporation-condensation without any additives.

Nitride-bonded silicon carbide (NBSC) is made by adding fine silicon powder with silicon carbide particles or eventually in the presence of a mineral additive and sintering in a nitrogen furnace. The silicon carbide is bonded by the silicon nitride phase ($Si_3N_4$) formed during nitriding.

Reaction bonded silicon carbide (RBSC), also known as siliconized silicon carbide or SiSiC, is a type of silicon carbide that is manufactured by a chemical reaction between porous carbon or graphite with molten silicon. The silicon reacts with the carbon forming silicon carbide and bonds the silicon carbide particles. Any excess silicon fills the remaining pores in the body and produces a dense SiC—Si composite. Due to the left-over traces of silicon, reaction bonded silicon carbide is often referred to as siliconized silicon carbide. The process is known variously as reaction bonding, reaction sintering, self-bonding, or melt infiltration.

In general, high purity SiC particles have resistivity above 1000 Ohm·cm, whereas sintered, reaction bonded and nitride-bonded can exhibit resistivities of about 100 to 1000 depending on the impurities in the SiC phase. Electrical resistivity of bulk polycrystalline SiC ceramics shows a wide range of resistivity depending on the sintering additive and heat-treatment conditions (Journal of the European Ceramic Society, Volume 35, Issue 15, December 2015, Pages 4137; Ceramics International, Volume 46, Issue 4, March 2020, Pages 5454). SiC polytypes with high purity possess high electrical resistivity ($>10^6$ Ω·cm) because of their large bandgap energies. However, the electrical resistivity of SiC is affected by doping impurities. N and P act as n-type dopants and decrease the resistivity of SiC, whereas Al, B, Ga, and Sc act as p-type dopants. SiC doped with Be, O, and V are highly insulating. N is considered the most efficient dopant for improving the electrical conductivity of SiC. For N doping of SiC (to decrease resistivity) $Y_2O_3$ and $Y_2O_3$-$REM_2O_3$ (REM, rare earth metal=Sm, Gd, Lu) have been used as sintering additives for efficient growth of conductive SiC grains containing N donors. N-doping in SiC grains was promoted by the addition of nitrides (AlN, BN, $Si_3N_4$, TiN, and ZrN) or combinations of nitrides and $Re_2O_3$ (AlN-$REM_2O_3$ (REM=Sc, Nd, Eu, Gd, Ho, and Er) or TiN—$Y_2O_3$).

The Reaction of Alkane Transformation into Olefin, Such as Alkane Partial Oxidation Reaction and/or Oxidative Coupling Reaction of Light Alkanes Embodiments of the invention are directed to a process for conversion/transformation of alkane, the process comprising contacting, under suitable reaction conditions, a reformer feed, or a combined feed, comprising at least one alkane and at least one oxidant and optionally at least one diluent. The one or more alkanes is or comprises methane.

The light alkane-containing feedstock may comprise one or more alkanes being methane and one or more selected from ethane ($C_2H_6$), propane ($C_3H_8$), butane ($C_4H_{10}$) and its structural isomers (e.g., n-butane and/or iso-butane), pentane ($C_5H_{12}$) and its structural isomers, higher molecular weight alkanes ($C_6$+alkanes), and any mixture thereof.

The light alkane-containing feedstock may further comprise one or more hydrocarbons selected from ethylene ($C_2H_4$), propylene ($C_3H_6$), butene ($C_4H_8$) and its structural and positional isomers (e.g., 1-butene, 2-butene, and/or iso-butylene), pentene ($C_5H_{10}$) and its structural and positional isomers, higher molecular weight hydrocarbons ($C_6$+ hydrocarbons) and any mixture thereof.

In an embodiment the light alkane-comprising feedstock with one or more alkane and one or more oxidants is obtained by mixing a stream comprising one or more alkanes selected from methane, ethane, propane, butane, iso-butane and any mixture thereof; with a stream comprising one or more oxidants selected from COS (carbonyl sulphide), $CO_2$ (carbon dioxide) and any mixture thereof. Said mixing can be made outside the at least one fluidized bed reactor or in situ (i.e. inside the at least one fluidized bed reactor).

With a preference, the alkane content in the light alkane-comprising feedstock suitable for alkane transformation to olefin comprises at least 5 vol. % based on the total volume of the light alkane-comprising feedstock, more preferably at least 15 vol. %. For example, the alkane content is at most 95 vol. % based on the total volume of light alkane-comprising feedstock.

For example, the content of methane in the light alkane-comprising feedstock is at least 5 vol. % based on the total volume of the light alkane-comprising feedstock, more preferably at least 15 vol. %. For example, the content of methane is at most 95 vol. % based on the total volume of light alkane-comprising feedstock.

The oxidant content, which might be a $CO_2$, COS, or mixture thereof, amounts to at least 5 vol. % of the total volume of the light alkane-comprising feedstock, more preferably at least 15 vol. %. For example, the oxidant content is at most 60 vol. % based on the total volume of light alkane-comprising feedstock.

The diluent might be nitrogen, argon, helium, xenon, or carbon monoxide. Preferably, the diluent content at most 70 vol. % based on the total volume of the light alkane-comprising feedstock, more preferably at most 30 vol. %, even more preferably less than 5 vol. %. In some embodiments, there is no diluent in the light alkane-comprising feedstock.

The reactions of oxidative coupling of methane with COS and $CO_2$ proceed as follows:

$$2CH_4+COS \rightarrow C_2H_4+2H_2S+2CO \; \Delta H=216.7 \text{ kJ}$$

$$2CH_4+COS \rightarrow C_2H_6+H_2S+CO \; \Delta H=73 \text{ kJ}$$

$$2CH_4+2CO_2 \rightarrow C_2H_4+2 \; H_2O+2CO \; \Delta H=71 \text{ kJ}$$

$$2CH_4+CO_2 \rightarrow C_2H_6+H_2O+CO \; \Delta H=72 \text{ KJ}$$

The reaction of partial oxidation includes possible transformation of alkanes into CO (also known as dry reforming) or $CS_2$ and oxidative dehydrogenation into corresponding olefins:

$$C_2H_6+COS \rightarrow C_2H_4+H_2S+CO \; \Delta H=143.5 \text{ kJ}$$

$$C_2H_6+7COS \rightarrow 2CS_2+3H_2S+7CO \; \Delta H=452.9 \text{ kJ}$$

$$CH_4+CO_2 \rightarrow 2CO+2H_2 \; \Delta H=247.8 \text{ kJ}$$

$$C_2H_6+2CO_2 \rightarrow 4CO+3H_2 \; \Delta H=429.8 \text{ KJ}$$

$$C_2H_6+CO_2 \rightarrow C_2H_4+H_2O+CO \; \Delta H=133.4 \text{ KJ}$$

$$C_2H_6+5CO_2 \rightarrow 3H_2O+7CO \; \Delta H=553.7 \text{ KJ}$$

Obtained effluent depending on the selection of feedstock composition and operating condition might contain unreacted alkanes, unreacted $CO_2$, unreacted COS, alkenes, $H_2S$, $H_2O$, $CS_2$, hydrogen, and carbon monoxide. The mixture could be separated by the techniques known in the art such as distillation, adsorption, absorption, membrane separation or flash-separation.

In one embodiment, the alkane transformation into olefin is performed in the absence of a catalytic composition.

For example, the alkane transformation into olefin is conducted at a temperature ranging from 500° C. to 2000° C., more preferably from 550° C. to 1700° C., even more preferably from 600° C. to 1500° C., or from 700° C. to 1300° C.; most preferably from 800° C. to 1200° C., or from 900° C. to 1400° C.; and even most preferably from 1000° C. to 1500° C.

For example, the said transformation into olefin is performed at a pressure ranging between 0.1 MPa and 5.0 MPa, preferably between 0.2 MPa and 3.0 MPa.

For example, the alkane transformation into olefin is conducted in presence of a reaction stream and is performed at a weight hourly space velocity of said reaction stream comprised between 0.1 h$^{-1}$ and 100 h$^{-1}$, preferably comprised between 1.0 h$^{-1}$ and 50 h$^{-1}$.

The residence time of the light alkane-comprising feedstock in the fluidised bed section of the reactor where the temperature is between 600 and 1500° C., may advantageously range from 0.01 to 0.6 seconds, more preferably from 0.1 to 0.3 seconds.

The Optional Particles of a Catalytic Composition

In an embodiment, the alkane transformation into olefin is performed on a catalyst composition. In such embodiment, the bed comprises electrically conductive particles and particles of a catalyst composition that can be the same or different.

For example, the content of the particles of a catalytic composition based on the total weight of the particles of the bed is ranging from 30 wt. % to 100 wt. %; preferably from 32 wt. % to 95 wt. %, more preferably from 35 wt. % to 90 wt. %, even more preferably from 37 wt. % to 85 wt. %, most preferably from 40 wt. % to 80 wt. %, even most preferably from 45 wt. % to 75 wt. % or from 50 wt. % to 70 wt. %. In the case where the content of the particles of a catalytic composition based on the total weight of the particles of the bed is 100 wt. %, at least a part of said particles of a catalytic composition are also electrically conductive In an embodiment, the catalyst composition comprises one or more selected from rare earth oxide, rare earth sulphides, transition metal oxides transition metal sulphides and any mixture thereof; wherein preferably the catalyst composition further comprises one or more dopants. The presence or not of dopants in the catalyst composition is depending on the choice of the oxidant used in the process. When the oxidant is COS, the presence of one or more dopants in the catalyst composition is optional. When the oxidant is $CO_2$, the catalyst composition must comprise one or more dopants.

Rare earth oxides are one or more selected from scandium (Sc), yttrium (Y), lanthanum (La), cerium (Ce), praseodymium (Pr), neodymium (Nd), promethium (Pm); samarium (Sm), europium (Eu), gadolinium (Gd), terbium (Tb), dysprosium (Dy), holmium (Ho), erbium (Er), thulium (Tm), ytterbium (Yb), lutetium, (Lu).

Transition metals are one or more selected from Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, Db, Sg, Bh, Hs, Mt, Ds, Rg, and Cn.

With preference, the one or more dopants are selected from Eu/Na, Sr/Na, Na/Zr/Eu/Ca, Mg/Na, Sr/Sm/Ho/Tm, Sr/W, Mg/La/K, Na/K/Mg/Tm, Sr/W, Na/Dy/K, Na/La/Dy, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ca/Cs, Ca/Mg/Na, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Gd/Ho/Sr, Ca/Sr, Ca/Sr/W, Na/Zr/Eu/Tm, Sr/Ho/Tm/Na, Sr/Pb, Ca, Sr/W/Li, Ca/Sr/W, Sr/Hf or combinations thereof.

Preferably, a catalyst composition is selected from one of the following, Na—W—Mn/SiO$_2$, NaCl—MnNa$_2$WO$_4$/SiO$_2$, La$_2$O$_3$—CeO$_2$, Li/MgO, CaO—Sm$_2$O$_3$, KCl—SmCl$_3$, CaO—NaCl/Na$_2$CO$_3$, CeO$_2$/ZnO, La$_2$O$_3$/Al$_2$O$_3$, FeS$_x$.

Metal-containing dopants could interact with oxidants present in the feedstream, namely COS and CO$_2$, according to the following equations:

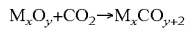

$$M_xO_y + CO_2 \rightarrow M_xCO_{y+2}$$

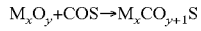

$$M_xO_y + COS \rightarrow M_xCO_{y+1}S$$

The reactions might be non-stoichiometric and/or involve anion disproportionation, leading to the formation of a phase of thiocarbonates (describes a family of anions with the general chemical formula $CS_{3-x}O_x^{2-}$ (x=0, 1, or 2)).

Therefore, in an embodiment said dopant comprises at least one alkali, alkali-eath, transition metal, post-transition metal or rare earth metal carbonate or thiocarbonate, or mixture thereof.

Catalyst composition could further comprise a support and/or binder. Suitable particulate catalyst supports are refractory oxides such as alumina (Al$_2$O$_3$), titania (TiO$_2$), zirconia (ZrO$_2$), hafnia (HfO$_2$), lanthania (La$_2$O$_3$), magnesia (MgO), ceria (CeO$_2$), yttria (Y$_2$O$_3$), preferably zirconia stabilized with magnesia, lanthania, yttria or ceria; metal-aluminates such as calcium aluminate and magnesium aluminate; and mixtures thereof. Particularly preferred particulate catalyst supports comprise alumina and/or stabilized zirconia, e.g. lanthania-stabilized alumina, ceria-zirconia-alumina, ceria-titania-alumina and ceria-magnesia-alumina materials.

Preferred support materials are those common materials (mentioned above) that can be used for resistive heating at the same time and which can be subdivided into two main groups: (1) Metallic alloys and (2) non-metallic resistors like silicon carbide (SiC) and molybdenum disilicide (MoSi$_2$), several mixed oxides with variable temperature optima and carbons like graphite. This latter option results in intimate contact between the catalytic active metal and the resistor particulate material.

The particulate catalyst support particles preferably have a particle size ranging from 5 to 300 μm, more preferably from 10 to 200 μm and most preferably from 30 and 150 μm. The catalyst may be dispersed over the surface of the particulate support by conventional impregnation of soluble metal compounds onto the particulate catalyst support followed by drying and calcination to convert the catalytic metal compound or compounds to their respective oxides. Followed by sulphidation in a stream of suitable sulphiding agent, e.g. H$_2$S or DMS, would lead to the formation of corresponding sulphides.

Alternatively, the catalytic metal or metal precursors may be dispersed over the surface of the particulate catalyst support material by precipitation, using metals sols or by deposition-precipitation methods employing metal salts that deposit insoluble metal compounds on the particulate catalyst support from solution upon heating. Further, metal salts can be ion-exchanged with counter cations on the support material. The metal precursors are reduced into the metallic state at elevated temperature by using hydrogen, carbon monoxide or hydrocarbons as reductants. This can be done before loading the catalyst in the fluidized bed reactor or in situ in the fluidized bed before feeding the feedstock or during feeding the feedstock.

Said catalyst composition could comprise a binder. With preference, one or more of the following can be used to further define the binder:

The binder is selected from silica, alumina, clays, alumina phosphates, calcium phosphates, magnesium phosphates, mullite and any mixture thereof.

The binder is or comprises silica.

The binder is present in an amount of at least 5 wt. % or of at least 10 wt. % as based on the total weight of the catalyst composition, preferably of at least 20 wt. %, most preferably of at least 30 wt. %, even more preferably of at least 40 wt. % and most preferably of at least 50 wt. %.

The binder is present in an amount ranging from 5 wt. % to 75 wt. % based on the total weight of said catalyst composition; preferably ranging from 10 to 75 wt. %; more preferably, ranging from 12 to 65 wt. %; even more preferably ranging from 15 to 60 wt. %; most preferably ranging from 18 to 50 wt. %; even most preferably ranging from 20 to 40 wt. %; for example, ranging from 15 to 30 wt. % or ranging from 10 to 50 wt. %.

The Installation

The terms "bottom" and "top" are to be understood in relation to the general orientation of the installation or the fluidized bed reactor. Thus, "bottom" will mean greater ground proximity than "top" along the vertical axis. In the different figures, the same references designate identical or similar elements.

FIG. 1 illustrates a prior art fluidized bed reactor 1 comprising a reactor vessel 3, a bottom fluid nozzle 5 for the introduction of a fluidizing gas and a light alkane-comprising feedstock, an optional inlet 7 for the material loading, an optional outlet 9 for the material discharge and a gas outlet 11 and a bed 15. In the fluidized bed reactor 1 of FIG. 1 the heat is provided by preheating the feedstock by combustion of fossil fuels using heating means 17 arranged for example at the level of the line that provides the reactor with the fluidizing gas and the light alkane-comprising feedstock.

The installation of the present disclosure is now described with reference to FIGS. 2 to 5. For sake of simplicity, internal devices are known by the person in the art that are used in fluidized bed reactors, like bubble breakers, deflectors, particle termination devices, cyclones, ceramic wall coatings, thermocouples, etc. . . . are not shown in the illustrations. FIGS. 2 to 5 illustrate the electrified fluidized bed unit.

Figure 2:
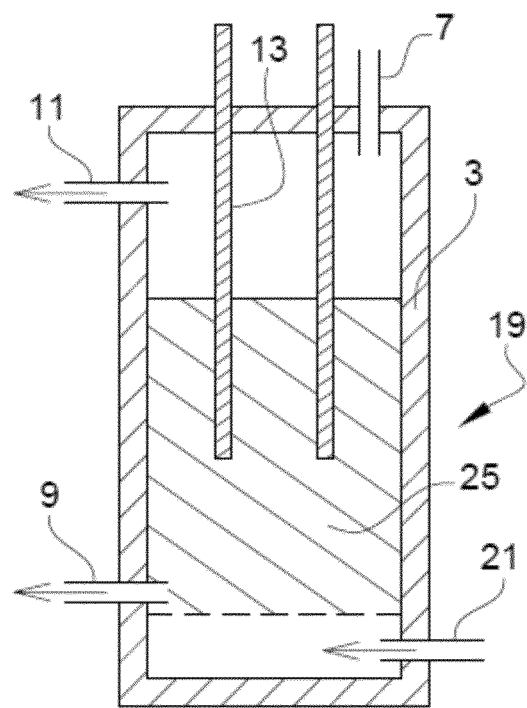
FIG. 2 illustrates an installation according to the disclosure with one reactor wherein the heating zone and reaction zone are the same.

FIG. 2 illustrates a first installation with a fluidized bed reactor 19 where the heating and reaction zone are the same. The fluidized bed reactor 19 comprises a reactor vessel 3, a bottom fluid nozzle 21 for the introduction of a fluidizing gas and a light alkane-comprising feedstock, an optional inlet 7 for the material loading, an optional outlet 9 for the material discharge and a gas outlet 11. The fluidized bed reactor 1 of FIG. 2 shows two electrodes 13 submerged in bed 25.

Figure 3:
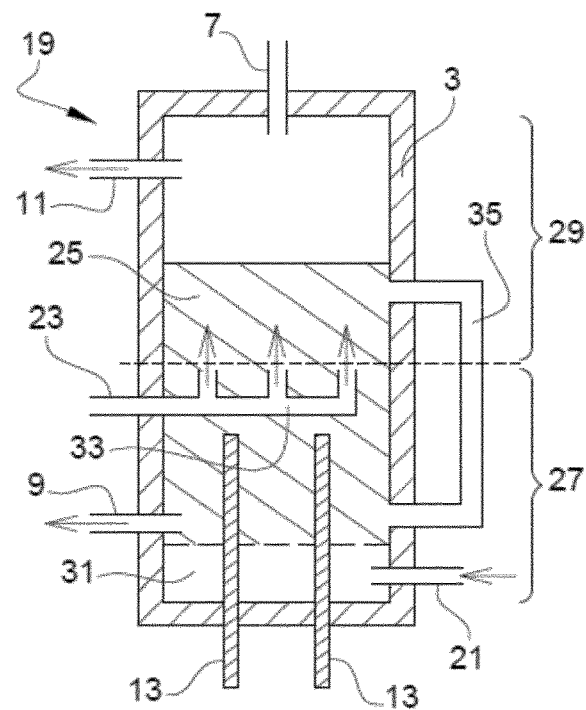
FIG. 3 illustrates an installation according to the disclosure with one reactor wherein the heating zone and reaction zone are arranged one above the other.

FIG. 3 illustrates an embodiment wherein at least one fluidized bed reactor 19 comprises a heating zone 27 and a reaction zone 29, with the heating zone 27 being the bottom zone and the reaction zone 29 being on top of the heating zone 27. One or more fluid nozzles 23 to provide a light alkane-comprising feedstock to the reaction zone from a distributor 33. As it can be seen in FIG. 3, the one or more fluid nozzles 23 can be connected to a distributor 33 to distribute the light alkane-comprising feedstock inside bed 25.

Figure 4:
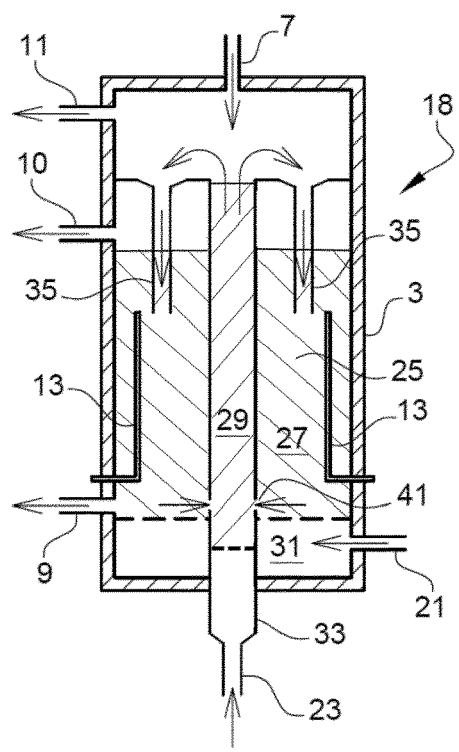
FIG. 4 illustrates an installation according to the disclosure with one reactor wherein the heating zone and reaction zone are arranged one lateral to the other.

FIG. 4 illustrates an installation wherein at least one fluidized bed reactor 18 comprises at least two lateral zones with the outer zone being the heating zone 27 and the inner zone being the reaction zone 29. The heated particles of the bed 25 from the outer zone are transferred to the inner zone by one or more openings 41 and mixed with the light alkane-comprising feedstock. At the end of the reaction zone, the particles are separated from the reaction product and transferred to the heating zone.

Figure 5:
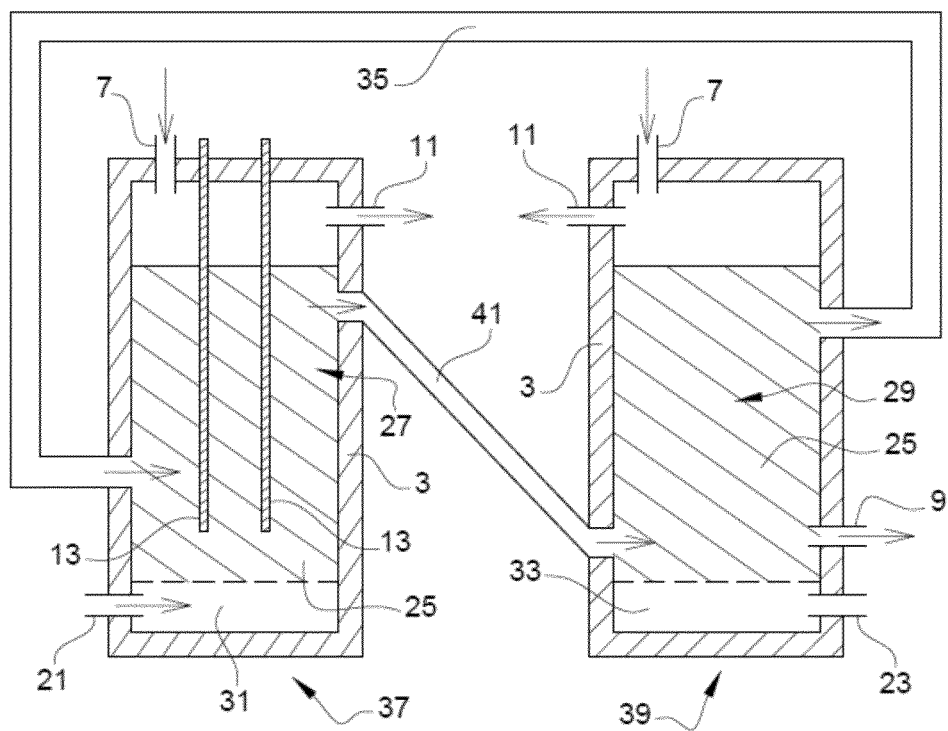
FIG. 5 illustrates an installation according to the disclosure with two reactors.

FIG. 5 illustrates the installation that comprises at least two fluidized bed reactors (37, 39) connected one to each other wherein at least one fluidized bed reactor is the heating zone 27 and one at least one fluidized bed reactor is the reaction zone 29.

The present disclosure provides for an installation to be used in a process to perform an alkane transformation into olefin, said installation comprises an electrified fluidized bed unit with at least one fluidized bed reactor (18, 19, 37, 39) comprising:
    at least two electrodes 13,
    a reactor vessel 3;
    one or more fluid nozzles (21, 23) for the introduction of a fluidizing gas and/or of a light alkane-comprising feedstock within at least one fluidized bed reactor (18, 19, 37, 39); and
    a bed 25 comprising particles;
wherein at least 10 wt. % of the particles of the bed based on the total weight of the particles of the bed 25 are electrically conductive, have a resistivity ranging from 0.001 Ohm·cm to 500 Ohm·cm at 800° C.

When the process to perform an alkane transformation into olefin also comprises a sub-step of production of a COS-containing stream, the installation to perform the alkane partial oxidation reaction and/or the oxidative coupling reaction of light alkanes comprises
    a $CO_2$ sulphuration unit comprising one or more conversion reactors,
    an optional separation unit,
    an electrified fluidized bed unit comprising at least one fluidized bed reactor (18, 19, 37, 39) comprising at least two electrodes 13; a reactor vessel 3; one or more fluid nozzles (21, 23) for the introduction of a fluidizing gas and/or of a stream of light alkane-comprising feedstock within at least one fluidized bed reactor; and a bed comprising particles; wherein at least 10 wt. % of the particles of the bed based on the total weight of the particle of the bed are electrically conductive, have a resistivity ranging from 0.001 Ohm·cm to 500 Ohm·cm at a temperature of 800° C.;
    and in that wherein the $CO_2$ sulphuration unit, the separation unit when present and the electrified fluidized bed unit are fluidically connected in series in the order mentioned.

For example, the electrically conductive particles of the bed are or comprise one or more selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

For example, the electrically conductive particles of the bed are or comprise one or more selected from one or more metallic alloys, one or more non-metallic resistors, one or more metallic carbides, one or more transition metal nitrides, one or more metallic phosphides, graphite, carbon black, one or more superionic conductors, one or more phosphate electrolytes, one or more mixed oxides being doped with one or more lower-valent cations, one or more mixed sulphides being doped with one or more lower-valent cations, and any mixture thereof.

In an embodiment, from 50 wt. % to 100 wt. % of the electrically conductive particles of the bed based on the total weight of the electrically conductive particles of the bed are one or more selected from graphite, carbon black, one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, one electrode is a submerged central electrode or two electrodes 13 are submerged within the reactor vessel 3 of at least one reactor (18, 19, 37).

For example, the fluidizing gas is one or more diluent gases.

In a preferred embodiment, the at least one fluidized bed reactor (18, 19, 37, 39) is devoid of heating means. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof. In a preferred embodiment, the at least one fluidized bed reactor comprising at least two electrodes and a bed comprising particles is devoid of structured packing such as honeycomb monoliths or crossed plate.

For example, the reactor vessel 3 has an inner diameter of at least 100 cm, or at least 200 cm; or at least 400 cm. Such a large diameter allows to carry out the chemical reaction at an industrial scale, for example at a weight hourly space velocity of said reaction stream comprised between 0.1 $h^{-1}$ and 100 $h^{-1}$, preferably comprised between 1.0 $h^{-1}$ and 50 $h^{-1}$. The weight hourly space velocity is defined as the ratio of mass flow of the reaction stream to the mass of solid particulate material in the fluidized bed.

The at least one fluidized bed reactor (18, 19, 37) comprises at least two electrodes 13. For example, one electrode is in electrical connection with the outer wall of the fluidized bed reactor, while one additional electrode is submerged into the fluidized bed 25, or both electrodes 13 are submerged into the fluidized bed 25. Said at least two electrodes 13 are electrically connected and can be connected to a power supply (not shown). It is advantageous that said at least two electrodes 13 are made of graphite. The person skilled in the art will have an advantage that the electrodes 13 are more conductive than the particle bed 25.

For example, at least one electrode 13 is made of or comprises graphite; preferably, all or the two electrodes 13 are made of graphite. For example, one of the electrodes is the reactor vessel, so that the reactor comprises two electrodes, one being the submerged central electrode and one being the reactor vessel 3.

For example, the at least one fluidized bed reactor comprises at least one cooling device arranged to cool at least one electrode.

During use of the fluidized bed reactor, an electric potential of at most 300 V is applied, preferably at most 250 V, more preferably at most 200 V, even more preferably at most 150 V, most preferably at most 100 V, even most preferably at most 90 V, or at most 80 V.

Thanks to the fact that the power of the electric current can be tuned, it is easy to adjust the temperature within the reactor bed.

The reactor vessel 3 can be made of graphite. In an embodiment, it can be made of electro-resistive material that is silicon carbide or a mixture of silicon carbide and graphite.

With preference, the reactor vessel 3 comprises a reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ). SiAlON ceramics are ceramics based on the elements silicon (Si), aluminium (Al), oxygen (O) and nitrogen (N). They are solid solutions of silicon nitride ($Si_3N_4$), where Si—N bonds are partly replaced with Al—N and Al—O bonds.

For example, the reactor vessel 3 is made of an electro-resistive material that is a mixture of silicon carbide and graphite; and the electro-resistive material of the reactor vessel 3 comprises from 10 wt. % to 99 wt. % of silicon carbide based on the total weight of the electro-resistive material; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the reactor vessel 3 is made of an electro-resistive material that is a mixture of silicon carbide and graphite.

For example, the reactor vessel 3 is not conductive. For example, the reactor vessel 3 is made of ceramic.

For example, the at least one fluidized bed reactor (18, 19, 37, 39) comprises a heating zone 27 and a reaction zone 29, one or more fluid nozzles 21 to provide a fluidizing gas to at least the heating zone from a distributor 31, one or more fluid nozzles 23 to provide a light alkane-comprising feedstock to the reaction zone from a distributor 33, and means 41 to transport the particles from the heating zone 27 to the reaction zone 29 when necessary, and optional means 35 to transport the particles from the reaction zone 29 back to the heating zone 27.

For example, as illustrated in FIG. 3, the at least one fluidized bed reactor is a single one fluidized bed reactor 19 wherein the heating zone 27 is the bottom part of the fluidized bed reactor 19 while the reaction zone 29 is the top part of the fluidised bed reactor 19; with preference, the installation comprises one or more fluid nozzles 23 to inject a light alkane-comprising feedstock between the two zones (27, 29) or in the reaction zone 29. The fluidized bed reactor 19 further comprises optionally an inlet 7 for the material loading, optionally an outlet 9 for the material discharge and a gas outlet 11. With preference, the fluidized bed reactor 19 is devoid of heating means. For example, the electrodes 13 are arranged at the bottom part of the fluidized bed reactor 19, i.e., in the heating zone 27. For example, the top part of the fluidised bed reactor 19, i.e., the reaction zone 29, is devoid of electrodes. Optionally, the fluidized bed reactor 19 comprises means 35 to transport the particles from the reaction zone 29 back to the heating zone 27; such as through a line arranged between the top part and the bottom part of the fluidized bed reactor 19.

For example, as illustrated in FIG. 4, the installation comprises at least two lateral fluidized bed zones (27, 29) connected one to each other wherein at least one fluidized bed zone 27 is the heating zone and at least one fluidized bed zone 29 is the reaction zone. For example, the heating zone 27 is surrounding the reaction zone 29. With preference, the installation comprises one or more fluid nozzles 23 arranged to inject a light alkane-comprising feedstock to the at least one reaction zone 29 using a distributor 33. The fluidized bed zones (27, 29) further comprise optionally an inlet 7 for the material loading and a gas outlet 11. With preference, the at least one fluidized bed zone being the heating zone 27 and/or the at least one fluidized bed zone being the reaction zone 29 is devoid of heating means. For example, the at least one fluidized bed zone being the reaction zone 29 shows optionally an outlet 9 for the material discharge. One or more fluid nozzles 21 provide a fluidizing gas to at least the heating zone from a distributor 31. With one or more inlet devices 41, heated particles are transported from the heating zone 27 to the reaction zone 29, and with one or more means 35 comprising downcomers, the separated particles are transported from the reaction zone 29 back to the heating zone 27. The fluidization gas for the heating zone 27 can be an inert diluent, like one or more selected from steam, hydrogen, carbon dioxide, methane, argon, helium and nitrogen. In such a configuration the fluidization gas for the heating zone can also comprise air or oxygen to burn deposited coke from the particles.

For example, as illustrated in FIG. 5, the installation comprises at least two fluidized bed reactors (37, 39) connected one to each other wherein at least one fluidized bed reactor 37 is the heating zone 27 and at least one fluidized bed reactor 39 is the reaction zone 29. With preference, the installation comprises one or more fluid nozzles 23 arranged to inject a light alkane-comprising feedstock to the at least one fluidized bed reactor 39 being the reaction zone 29. The fluidized bed reactors (37, 39) further comprise optionally an inlet 7 for the material loading and a gas outlet 11. With preference, the at least one fluidized bed reactor 37 being the heating zone 27 and/or the at least one fluidized bed reactor 39 being the reaction zone 29 is devoid of heating means. For example, the at least one fluidized bed reactor 39 being the reaction zone 29 shows optionally an outlet 9 for the material discharge. Through the inlet device 41, heated particles are transported from the heating zone 27 to the reaction zone 29 when necessary, and using device 35, the separated particles after the reaction zone are transported from the reaction zone back to the heating zone. The fluidization gas for the heating zone can be an inert diluent, like one or more selected from steam, hydrogen, carbon dioxide, methane, argon, helium, and nitrogen. In such a configuration the fluidization gas for the heating zone can also comprise air or oxygen to burn deposited coke from the particles.

For example, the at least one fluidized bed reactor 37 being the heating zone 27 comprises at least two electrodes 13 whereas the at least one fluidized bed reactor 39 being the reaction zone 29 is devoid of electrodes.

For example, the at least two fluidized bed reactors (37, 39) are connected one to each other by means 41 suitable to transport the particles from the heating zone 27 to the reaction zone 29, such as one or more lines.

For example, the at least two fluidized bed reactors (37, 39) are connected one to each other by means 35 suitable to transport the particles from the reaction zone 29 back to the heating zone 27, such as one or more lines.

The invention claimed is:

1. A process to perform an alkane transformation into olefin; said process comprising the steps of:
    a) providing a stream of light alkane-comprising feedstock comprising one or more alkanes selected from methane, ethane, propane, butane, isobutane and any mixture thereof and one or more oxidants selected from carbon dioxide, carbonyl sulphide and any mixture thereof, wherein oxidant content amounts least 15 vol. % based on the total volume of the light alkane-comprising feedstock; and further providing at least one fluidized bed reactor comprising at least two electrodes and a bed comprising particles;
    b) putting the particles of the bed in a fluidized state to obtain a fluidized bed;
    c) heating the fluidized bed to a temperature ranging from 600° C. to 1500° C. to conduct the transformation into olefin on the light alkane-comprising feedstock; and
    d) optionally, recovering the products of the reaction;
characterized in that the step c) of heating the fluidized bed is performed by passing an electric current through the fluidized bed; in that the particles of the bed comprise electrically conductive particles and particles of a catalytic composition; in that, at least 10 wt. % of the particles based on the total weight of the particles of the bed are electrically conductive particles and have a resistivity ranging from 0.001 Ohm·cm to 500 Ohm·cm at 800° C.; in that the void fraction of the bed is ranging from 0.5 to 0.8 and the particles of the bed have an average particle size ranging from 5 to 300 μm as determined by sieving according to ASTM D4513-11;
and in that the catalyst composition comprises one or more selected from rare earth oxides, rare earth sulphides, transition metal oxides, and any mixture thereof and/or one or more selected from Na—W—Mn/$SiO_2$, NaCl—Mn$Na_2WO_4$/$SiO_2$, $La_2O_3$—$CeO_2$, Li/MgO, CaO—$Sm_2O_3$, KCl—$SmCl_3$, CaO—NaCl/$Na_2CO_3$, $CeO_2$/ZnO, $La_2O_3$/$Al_2O_3$ and $FeS_x$, the catalyst composition further comprising one or more dopants when one oxidant of the light alkane-comprising feedstock is carbon dioxide.

2. The process according to claim 1, characterized in that the electrically conductive particles of the bed are one or more selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

3. The process according to claim 1, characterized in that the electrically conductive particles of the bed comprise one or more carbon-containing particles being graphite and/or in that the electrically conductive particles of the bed comprise one or more non-metallic resistors selected from silicon carbide, molybdenum disilicide or a mixture thereof.

4. The process according to claim 1, characterized in that the electrically conductive particles of the bed comprise a mixture of a non-metallic resistor being silicon carbide and electrically conductive particles different from silicon carbide; with preference:
    the electrically conductive particles of the bed comprise from 10 wt. % to 99 wt. % of silicon carbide based on the total weight of the electrically conductive particles of the bed; and/or
    the said electrically conductive particles different from silicon carbide are one or more carbon-containing particles and/or one or more mixed oxides being doped with one or more lower-valent cations and/or one or more mixed sulphides being doped with one or more lower-valent cations.

5. The process according to claim 1, characterized in that the electrically conductive particles of the bed comprise one or more mixed oxides being doped with one or more lower-valent cations, the mixed oxides are selected from:
    one or more oxides having a cubic fluorite structure being at least partially substituted with one or more lower-valent cations selected from Sm, Gd, Y, Sc, Yb, Mg, Ca, La, Dy, Er, Eu; and/or
    one or more $ABO_3$-perovskites with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or
    one or more $ABO_3$-perovskites with A bivalent cation and B tetra-valent cation, being at least partially substituted with one or more lower-valent cations selected from Mg, Sc, Y, Nd or Yb in the B position or with a mixture of different B elements in the B position; and/or
    one or more $A_2B_2O_7$-pyrochlores with A trivalent cation and B tetra-valent cation being at least partially substituted in A position with one or more lower-valent cations selected from Ca or Mg, and comprising at least one of Sn, Zr and Ti in B position.

6. The process according to claim 1, characterized in that the electrically conductive particles of the bed comprise
    a. one or more metallic alloys; and/or
    b. one or more superionic conductors, one or more superionic conductors are selected from $LiAlSiO_4$, $Li_{10}GeP_2S_{12}$, $Li_{3.6}Si_{0.6}P_{0.4}O_4$, sodium superionic conductors, or sodium beta alumina.

7. The process according to claim 1, characterized in that the catalyst composition comprises one or more selected from rare earth oxides, rare earth sulphides, transition metal oxides transition metal sulphides and any mixture thereof and in that the catalyst composition comprises one or more dopants, the one or more dopants comprise at least one alkali, alkali-earth, transition metal, post-transition metal or rare earth metal carbonate or thiocarbonate, or any mixture thereof.

8. The process according to claim 1, characterized in that the void fraction of the bed is ranging from 0.5 to 0.7.

9. The process according to claim 1, characterized in that the particles of the bed have an average particle size ranging from 10 to 200 μm as determined by sieving according to ASTM D4513-11.

10. The process according to claim 1, characterized in that in step b) the particles of the bed are put in a fluidized state by passing upwardly through the said bed a gaseous stream comprising methane; and/or in that it comprises a step of pre-heating with a gaseous stream the one or more fluidized bed reactors before conducting said alkane partial oxidation reaction and/or oxidative coupling reaction in the fluidized bed reactor, wherein the gaseous stream has a temperature comprised between 400° C. and 1000° C.

11. The process according to claim 1, characterized in that the at least one fluidized bed reactor provided in step a) comprises a heating zone and a reaction zone and wherein the step c) of heating the fluidized bed to a temperature ranging from 600° C. to 1500° C. to conduct the alkane partial oxidation reaction and/or oxidative coupling reaction comprises the following sub-steps:
- heating the fluidized bed to a temperature ranging from 600° C. to 1500° C. by passing an electric current through the heating zone of the at least one fluidized bed,
- transporting the heated particles from the heating zone to the reaction zone,
- in the reaction zone, putting the heated particles in a fluidized state by passing upwardly through the said bed of the reaction zone a stream comprising a light alkane-comprising feedstock and optional diluent gases to obtain a fluidized bed to conduct the alkane transformation into olefin on the light alkane-comprising feedstock,
- optionally, recovering the particles from the reaction zone and recycling them to the heating zone.

12. The process according to claim 1, characterized in that the at least one fluidized bed reactor provided in step a) comprises a heating zone and a reaction zone and the step c) of heating the fluidized bed to a temperature ranging from 600° C. to 1500° C. to conduct the alkane transformation into olefin comprises the following sub-steps:
- pre-heating the fluidized bed to ranging from 400° C. and 1000° C. by passing upwardly through the particles bed a fluidizing stream being a gaseous stream having a temperature ranging from 400° C. and 1000° C.;
- heating the fluidized bed to a temperature ranging from 600° C. to 1500° C. by passing an electric current through the heating zone,
- transporting the heated particles from the heating zone to the reaction zone,
- in the reaction zone, putting the heated particles in a fluidized state by passing upwardly through the said bed of the reaction zone a stream comprising a light alkane-comprising feedstock and optional diluent gases to obtain a fluidized bed and to conduct the alkane transformation into olefin on the light alkane-comprising feedstock,
- optionally, recovering the particles from the reaction zone and recycling them to the heating zone.

13. The process according to claim 1, characterized in that step a) comprises a sub-step of production of a COS-containing stream, wherein said sub-step comprises providing feedstream containing at least 30 wt. % of carbon dioxide and at least 20 wt. % of hydrogen sulphide based on the total weight of said feedstream and converting said feedstream into a COS-containing stream; wherein the conversion is performed at a temperature ranging from 50 to 800° C., at a pressure ranging from 0.01 to 5 MPa and at a GHSV ranging from 0.1 to 10 $h^{-1}$ wherein the COS-containing stream is containing water and at least 10 wt. % of carbonyl sulphide (COS) based on the total weight of said COS-containing stream; with preference, the sub-step of production of a COS-containing stream is performed in presence of a COS-conversion catalyst and at least one sorbent.

* * * * *